(12) United States Patent
Bannigan et al.

(10) Patent No.: US 11,458,025 B2
(45) Date of Patent: *Oct. 4, 2022

(54) VERTEBRAL BODY REPLACEMENT

(71) Applicant: NuVasive, Inc., San Diego, CA (US)

(72) Inventors: Shaeffer Bannigan, San Diego, CA (US); Ryan Donahoe, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 454 days.

This patent is subject to a terminal disclaimer.

(21) Appl. No.: 16/510,123

(22) Filed: Jul. 12, 2019

(65) Prior Publication Data
US 2019/0328542 A1 Oct. 31, 2019

Related U.S. Application Data

(63) Continuation of application No. 15/635,087, filed on Jun. 27, 2017, now Pat. No. 10,390,960, which is a
(Continued)

(51) Int. Cl.
A61F 2/44 (2006.01)
A61F 2/46 (2006.01)
(Continued)

(52) U.S. Cl.
CPC .............. A61F 2/4455 (2013.01); A61F 2/44 (2013.01); A61F 2/4611 (2013.01);
(Continued)

(58) Field of Classification Search
CPC ............................................ A61F 2002/4415
See application file for complete search history.

(56) References Cited

U.S. PATENT DOCUMENTS 1,238,863 A 9/1917 Willour
1,486,723 A 3/1924 Bemson
(Continued)

FOREIGN PATENT DOCUMENTS

CA 2015507 1/1999
EP 369603 5/1990
(Continued)

OTHER PUBLICATIONS

Alleyne, Cargill, H., et al., "Current and future approaches to lumbar disc surgery: A literature review", Medscape Orthopedics & Sports Medicine, 1, [www.medscape.com/Medscape/OrthoSportsMed/1997/v01 .nll/.../mos3057], (1997).
(Continued)

Primary Examiner — Andrew Yang
(74) Attorney, Agent, or Firm — Hoffman Warnick LLC

(57) ABSTRACT

The present invention involves a system and methods for assembling and implanting a vertebral body implant. The vertebral body implant includes, but is not necessarily limited to, an expandable core body and endplates that can be attached at both ends. Endplates of various shapes, sizes and angles are attachable to the expandable core in a plurality of positions so that a suitable vertebral body implant can be implanted between vertebrae from an anterior, anterior-lateral, lateral, posterior or posterior-lateral approach.

20 Claims, 16 Drawing Sheets

Related U.S. Application Data continuation of application No. 14/177,100, filed on Feb. 10, 2014, now Pat. No. 9,687,357, which is a continuation of application No. PCT/US2012/050218, filed on Aug. 9, 2012, said application No. 14/177,100 is a continuation-in-part of application No. 12/661,206, filed on Mar. 12, 2010, now Pat. No. 9,387,090.

(60) Provisional application No. 61/521,704, filed on Aug. 9, 2011, provisional application No. 61/159,792, filed on Mar. 12, 2009, provisional application No. 61/260,375, filed on Nov. 11, 2009.

(51) Int. Cl.
  *A61F 2/28* (2006.01)
  *A61F 2/30* (2006.01)

(52) U.S. Cl.
  CPC ..... *A61F 2/4603* (2013.01); *A61F 2002/2835* (2013.01); *A61F 2002/305* (2013.01); *A61F 2002/3055* (2013.01); *A61F 2002/30171* (2013.01); *A61F 2002/30235* (2013.01); *A61F 2002/30383* (2013.01); *A61F 2002/30393* (2013.01); *A61F 2002/30395* (2013.01); *A61F 2002/30405* (2013.01); *A61F 2002/30433* (2013.01); *A61F 2002/30507* (2013.01); *A61F 2002/30556* (2013.01); *A61F 2002/30579* (2013.01); *A61F 2002/30593* (2013.01); *A61F 2002/30601* (2013.01); *A61F 2002/30774* (2013.01); *A61F 2002/30777* (2013.01); *A61F 2002/30779* (2013.01); *A61F 2002/30785* (2013.01); *A61F 2002/30789* (2013.01); *A61F 2002/30818* (2013.01); *A61F 2002/30836* (2013.01); *A61F 2002/30841* (2013.01); *A61F 2002/4622* (2013.01); *A61F 2002/4627* (2013.01); *A61F 2002/4628* (2013.01); *A61F 2310/00017* (2013.01); *A61F 2310/00023* (2013.01)

(56) References Cited

U.S. PATENT DOCUMENTS

| | | |
|---|---|---|
| 1,896,715 A | 2/1933 | Martinetti |
| 3,486,505 A | 12/1969 | Morrison |
| 3,518,993 A | 7/1970 | Blake |
| 3,604,487 A | 9/1971 | Gilbert |
| 3,745,995 A | 7/1973 | Kraus |
| 3,848,601 A | 11/1974 | Ma et al. |
| 3,867,728 A | 2/1975 | Stubstad et al. |
| 4,026,304 A | 5/1977 | Levy |
| 4,026,305 A | 5/1977 | Brownlee et al. |
| 4,501,269 A | 2/1985 | Bagby |
| 4,545,374 A | 10/1985 | Jacobson |
| 4,646,738 A | 3/1987 | Trott |
| 4,657,550 A | 4/1987 | Daher |
| 4,743,256 A | 5/1988 | Brantigan |
| 4,781,591 A | 11/1988 | Allen |
| 4,834,757 A | 5/1989 | Brantigan |
| 4,877,020 A | 10/1989 | Vich |
| 4,878,915 A | 11/1989 | Brantigan |
| 4,932,975 A | 6/1990 | Main et al. |
| 4,950,296 A | 8/1990 | McIntyre |
| 4,961,740 A | 10/1990 | Ray et al. |
| 4,962,766 A | 10/1990 | Herzon |
| 5,015,247 A | 5/1991 | Michelson |
| 5,026,373 A | 6/1991 | Ray et al. |
| 5,047,055 A | 9/1991 | Bao et al. |
| 5,055,104 A | 10/1991 | Ray |
| 5,062,845 A | 11/1991 | Kuslich et al. |
| 5,071,437 A | 12/1991 | Steffee |
| 5,092,572 A | 3/1992 | Litwak et al. |
| 5,133,717 A | 7/1992 | Chopin |
| 5,133,755 A | 7/1992 | Brekke |
| 5,171,278 A | 12/1992 | Pisharodi |
| 5,192,327 A | 3/1993 | Brantigan |
| 5,217,497 A | 6/1993 | Mehdian |
| 5,236,460 A * | 8/1993 | Barber .................. A61F 2/4611 623/17.15 |
| 5,263,953 A | 11/1993 | Bagby |
| 5,269,785 A | 12/1993 | Bonutti |
| 5,284,153 A | 2/1994 | Raymond et al. |
| 5,290,494 A | 3/1994 | Coombes et al. |
| 5,300,076 A | 4/1994 | Lerich |
| 5,304,210 A | 4/1994 | Crook |
| 5,306,307 A | 4/1994 | Senter et al. |
| 5,306,309 A | 4/1994 | Wagner et al. |
| 5,322,505 A | 6/1994 | Krause et al. |
| 5,334,205 A | 8/1994 | Cain |
| 5,336,223 A | 8/1994 | Rogers |
| 5,364,400 A | 11/1994 | Rego, Jr. et al. |
| 5,395,372 A | 3/1995 | Holt et al. |
| 5,397,363 A | 3/1995 | Gelbard |
| 5,397,364 A | 3/1995 | Kozak |
| 5,405,391 A | 4/1995 | Henderson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,480,442 A | 1/1996 | Bertagnoli |
| 5,484,403 A | 1/1996 | Yoakum et al. |
| 5,484,437 A | 1/1996 | Michelson |
| 5,489,307 A | 2/1996 | Kuslich et al. |
| 5,489,308 A | 2/1996 | Kuslich et al. |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,688 A | 7/1996 | Navas |
| 5,545,222 A | 8/1996 | Bonutti |
| 5,562,736 A | 10/1996 | Ray et al. |
| 5,565,005 A | 10/1996 | Erickson et al. |
| 5,571,190 A | 11/1996 | Ulrich |
| 5,571,192 A | 11/1996 | Schonhoffer |
| 5,575,790 A | 11/1996 | Chen et al. |
| 5,593,409 A | 1/1997 | Michelson |
| 5,609,636 A | 3/1997 | Kohrs et al. |
| 5,611,800 A | 3/1997 | Davis et al. |
| 5,611,810 A | 3/1997 | Arnold et al. |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisdharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,676,703 A | 10/1997 | Gelbard |
| 5,683,394 A | 11/1997 | Rinner |
| 5,683,400 A | 11/1997 | McGuire |
| 5,683,464 A | 11/1997 | Wagner et al. |
| 5,690,629 A | 11/1997 | Asher et al. |
| 5,693,100 A | 12/1997 | Pisharodi |
| 5,700,264 A | 12/1997 | Zucherman et al. |
| 5,700,291 A | 12/1997 | Kuslich et al. |
| 5,700,292 A | 12/1997 | Marguiles |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi et al. |
| 5,707,373 A | 1/1998 | Sevrain et al. |

(56) References Cited

U.S. PATENT DOCUMENTS

| | | |
|---|---|---|
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,723,013 A | 3/1998 | Jeanson et al. |
| 5,728,159 A | 3/1998 | Stroever et al. |
| 5,741,253 A | 4/1998 | Michelson |
| 5,741,261 A | 4/1998 | Moskovitz et al. |
| 5,755,797 A | 5/1998 | Baumgartner |
| 5,766,252 A | 6/1998 | Henry et al. |
| 5,772,661 A | 6/1998 | Michelson |
| 5,775,331 A | 7/1998 | Raymond et al. |
| 5,775,797 A | 7/1998 | Henstra |
| 5,776,197 A | 7/1998 | Rabbe et al. |
| 5,776,198 A | 7/1998 | Rabbe et al. |
| 5,779,642 A | 7/1998 | Nightengale |
| 5,782,830 A | 7/1998 | Farris |
| 5,782,919 A | 7/1998 | Zdeblick et al. |
| 5,785,710 A | 7/1998 | Michelson |
| 5,797,909 A | 8/1998 | Michelson |
| 5,800,549 A | 9/1998 | Bao et al. |
| 5,800,550 A | 9/1998 | Sertich |
| 5,814,084 A | 9/1998 | Grivas et al. |
| 5,851,208 A | 12/1998 | Trott |
| 5,860,973 A | 1/1999 | Michelson |
| 5,865,845 A | 2/1999 | Thalgott |
| 5,865,848 A | 2/1999 | Baker |
| 5,885,299 A | 3/1999 | Winslow et al. |
| 5,888,219 A | 3/1999 | Bonutti |
| 5,888,224 A | 3/1999 | Beckers et al. |
| 5,893,890 A | 4/1999 | Pisharodi |
| 5,904,719 A | 5/1999 | Errico et al. |
| 5,910,315 A | 6/1999 | Stevenson et al. |
| 5,942,698 A | 8/1999 | Stevens |
| 5,954,769 A | 9/1999 | Rosenlicht |
| 5,968,098 A | 10/1999 | Winslow |
| 5,989,290 A | 11/1999 | Biedermann et al. |
| 5,993,474 A | 11/1999 | Ouchi |
| 6,003,426 A | 12/1999 | Kobayashi et al. |
| 6,004,326 A | 12/1999 | Castro et al. |
| 6,008,433 A | 12/1999 | Stone |
| 6,015,436 A | 1/2000 | Schonhoffer |
| 6,033,405 A | 3/2000 | Winslow et al. |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |
| 6,059,829 A | 5/2000 | Schlapfer et al. |
| 6,063,088 A | 5/2000 | Winslow |
| 6,083,225 A | 7/2000 | Winslow et al. |
| 6,096,080 A | 8/2000 | Nicholson et al. |
| 6,102,948 A | 8/2000 | Brosnahan, III |
| 6,120,503 A | 9/2000 | Michelson |
| 6,120,506 A | 9/2000 | Kohrs et al. |
| 6,132,472 A | 10/2000 | Bonutti |
| 6,143,033 A | 11/2000 | Paul et al. |
| 6,159,211 A | 12/2000 | Boriani et al. |
| 6,159,215 A | 12/2000 | Urbahns et al. |
| 6,176,881 B1 | 1/2001 | Schar et al. |
| 6,190,413 B1 | 2/2001 | Sutcliffe |
| 6,193,756 B1 | 2/2001 | Studer et al. |
| 6,200,347 B1 | 3/2001 | Anderson |
| 6,200,348 B1 | 3/2001 | Biedermann et al. |
| 6,214,050 B1 | 4/2001 | Huene |
| 6,224,607 B1 | 5/2001 | Michelson |
| 6,224,631 B1 | 5/2001 | Kohrs |
| 6,241,769 B1 | 6/2001 | Nicholson et al. |
| 6,241,771 B1 | 6/2001 | Gresser et al. |
| 6,251,140 B1 | 6/2001 | Marino et al. |
| 6,258,125 B1 | 7/2001 | Paul et al. |
| 6,277,149 B1 | 8/2001 | Boyle et al. |
| 6,296,665 B1 | 10/2001 | Strnad et al. |
| 6,319,257 B1 | 11/2001 | Carignan et al. |
| 6,344,057 B1 | 2/2002 | Rabbe et al. |
| 6,352,556 B1 | 3/2002 | Kretschmer et al. |
| 6,371,989 B1 | 4/2002 | Chauvin et al. |
| 6,383,221 B1 | 5/2002 | Scarborough et al. |
| 6,409,766 B1 | 6/2002 | Brett |
| 6,425,772 B1 | 7/2002 | Bernier et al. |
| 6,432,140 B1 | 8/2002 | Lin |
| 6,440,142 B1 | 8/2002 | Ralph et al. |
| 6,442,814 B1 | 9/2002 | Landry et al. |
| 6,447,547 B1 | 9/2002 | Michelson |
| 6,454,806 B1 | 9/2002 | Cohen et al. |
| 6,468,311 B2 | 10/2002 | Boyd et al. |
| 6,491,724 B1 | 12/2002 | Ferree |
| 6,524,341 B2 | 2/2003 | Lang et al. |
| 6,527,773 B1 | 3/2003 | Lin et al. |
| D472,634 S | 4/2003 | Anderson |
| D473,650 S | 4/2003 | Anderson |
| 6,547,823 B2 | 4/2003 | Scarborough et al. |
| 6,595,998 B2 | 7/2003 | Johnson et al. |
| 6,626,905 B1 | 9/2003 | Schmiel et al. |
| 6,635,086 B2 | 10/2003 | Lin |
| 6,648,895 B2 | 11/2003 | Burkus et al. |
| 6,672,019 B1 | 1/2004 | Wenz |
| 6,676,703 B2 | 1/2004 | Biscup |
| 6,706,067 B2 | 3/2004 | Shimp et al. |
| 6,730,088 B2 | 5/2004 | Yeh |
| 6,743,255 B2 | 6/2004 | Ferree |
| 6,746,484 B1 | 6/2004 | Liu et al. |
| 6,755,841 B2 | 6/2004 | Fraser et al. |
| 6,761,739 B2 | 7/2004 | Shepard |
| 6,824,564 B2 | 11/2004 | Crozet |
| 6,866,682 B1 | 3/2005 | An et al. |
| D503,801 S | 4/2005 | Jackson |
| 6,896,517 B1 | 5/2005 | Bjorn et al. |
| 6,902,579 B2 | 6/2005 | Harms et al. |
| 6,923,814 B1 | 8/2005 | Hildebrand et al. |
| 6,942,698 B1 | 9/2005 | Jackson |
| 6,964,687 B1 | 11/2005 | Bernard et al. |
| 6,979,353 B2 | 12/2005 | Bresina |
| 6,984,245 B2 | 1/2006 | McGahan et al. |
| 6,986,788 B2 | 1/2006 | Paul et al. |
| 6,989,031 B2 | 1/2006 | Michelson |
| 7,018,416 B2 | 3/2006 | Hanson et al. |
| 7,022,138 B2 | 4/2006 | Mashburn |
| 7,056,343 B2 | 6/2006 | Schafer et al. |
| D530,423 S | 10/2006 | Miles et al. |
| D594,986 S | 6/2009 | Miles et al. |
| D599,019 S | 8/2009 | Pimenta et al. |
| 7,621,953 B2 | 11/2009 | Braddock, Jr. et al. |
| 7,641,693 B2 | 1/2010 | Gutlin et al. |
| D621,509 S | 8/2010 | Lovell |
| 7,914,581 B2 | 3/2011 | Dickson |
| 7,918,891 B1 | 4/2011 | Curran et al. |
| 8,268,002 B2 | 9/2012 | Blackwell |
| 8,992,617 B2 * | 3/2015 | Woodburn ............... A61F 2/44 623/17.15 |
| 2002/0058950 A1 | 5/2002 | Winterbottom et al. |
| 2002/0082695 A1 | 6/2002 | Neumann |
| 2003/0105528 A1 | 6/2003 | Shimp et al. |
| 2003/0139812 A1 | 7/2003 | Garcia et al. |
| 2004/0153155 A1 | 8/2004 | Chung et al. |
| 2004/0186569 A1 | 9/2004 | Berry |
| 2005/0060034 A1 * | 3/2005 | Berry ..................... A61F 2/44 623/17.11 |
| 2005/0090898 A1 | 4/2005 | Berry |
| 2005/0107878 A1 | 5/2005 | Conchy |
| 2005/0143820 A1 | 6/2005 | Zucherman et al. |
| 2005/0197702 A1 | 9/2005 | Coppes et al. |
| 2006/0058879 A1 | 3/2006 | Metz-Stavenhagen |
| 2006/0100710 A1 | 5/2006 | Gutlin et al. |
| 2006/0129241 A1 | 6/2006 | Boyer, II et al. |
| 2006/0235528 A1 | 10/2006 | Buettner-Janz |
| 2006/0241770 A1 | 10/2006 | Rhoda et al. |
| 2007/0028710 A1 | 2/2007 | Kraus et al. |
| 2007/0129805 A1 | 6/2007 | Braddock, Jr. et al. |
| 2007/0191945 A1 | 8/2007 | Yu et al. |
| 2008/0114467 A1 | 5/2008 | Capote et al. |
| 2009/0112324 A1 | 4/2009 | Refai |
| 2009/0138089 A1 | 5/2009 | Doubler et al. |
| 2010/0076559 A1 | 3/2010 | Bagga et al. |

(56) References Cited

U.S. PATENT DOCUMENTS

| | | |
|---|---|---|
| 2010/0106251 A1 | 4/2010 | Kast |
| 2011/0106258 A1 | 5/2011 | Blackwell et al. |
| 2011/0218631 A1 | 9/2011 | Woodburn, Sr. |

FOREIGN PATENT DOCUMENTS

| | | |
|---|---|---|
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| EP | 1080703 | 3/2000 |
| WO | 90/00037 | 1/1990 |
| WO | 91/06261 | 5/1992 |
| WO | 92/14423 | 9/1992 |
| WO | 94/04100 | 3/1994 |
| WO | 94/10928 | 5/1994 |
| WO | 95/01810 | 1/1995 |
| WO | 96/08205 | 3/1996 |
| WO | 96/17564 | 6/1996 |
| WO | 96/41582 | 12/1996 |
| WO | 97/20513 | 6/1997 |
| WO | 97/33525 | 9/1997 |
| WO | 97/37620 | 10/1997 |
| WO | 98/09586 | 3/1998 |
| WO | 98/14142 | 4/1998 |
| WO | 98/17208 | 4/1998 |
| WO | 98/25539 | 6/1998 |
| WO | 99/08627 | 2/1999 |
| WO | 99/38461 | 8/1999 |
| WO | 00/45712 | 8/2000 |
| WO | 00/45713 | 8/2000 |
| WO | 01/41681 | 6/2001 |
| WO | 01/49333 | 7/2001 |
| WO | 04/210312 | 10/2004 |
| WO | 04/100837 | 11/2004 |
| WO | 05/037134 | 4/2005 |
| WO | 13/025448 | 2/2013 |

OTHER PUBLICATIONS

Benini, et al., "Undercutting decompression and posterior fusion with translaminar facet screw fixation in degenerative lumbar spinal stenosis: Technique and results", Neuro-Orthopedics, 17/18, 159-172 (1995).
Kambin, et al., "History and current status of percutaneous arthroscopic disc surgery", Spine, 21(24S):57S-61S (1996).
Stein, et al., "Percutaneous facet joint fusion: Preliminary experience", Journal of Vascular and Interventional Radiology, 4:69-74 (1993).
Vamvanij, et al., "Surgical treatment of internal disc disruption: An outcome study of four fusion techniques", Journal of Spinal Disorders, 11(5):375-382 (1998).
Baulot, et al., "Complementary anterior spondylodesis by thoracoscopy. Technical note regarding an observation", Lyon Surg., 90(5):347-351 (1994).
Berry, et al., "A morphometric study of human lumbar and selected thoracic vertebrae, study of selected vertebrae" Spine 12(4):362-367 (1996).
Crock, H. V., "A Short Practice of Spinal Surgery", Second, revised edition, published by Springer-Verlag/Wein, New York (1993).
Crock. H. V., "Anterior Lumbar Interbody Fusion" Clinical Orthopaedics & Related Research, Marshall R. Urist, Editor-in-Chief, J. B. Lippincott Company (1982).
Edeland, H.G., "Some additional suggestions for an intervertebral disc prosthesis", Journal of Biomedical Engineering, 7:57-62 (1985).
Kemp, H. B. S., "Anterior fusion of the spine for infective lesions in adults", Journal of Bone & Joint Surgery, 558(4):715-734 (1973).
Nuvasive, Inc., Corrected Final Invalidity Contentions Regarding U.S. Pat. No. 5,860,973, U.S. Pat. No. 6,592,586 and U.S. Pat. No. 6,945,933 filed in the United States District Court, Southern District of California on Jun. 14, 2010 (and 23 appendices).
CoRoent™ Marketing Brochure (9004001 A.0), NuVasive, Inc., 2004, 2 pages.
CoRoent™ Marketing Brochure (9004001 C.0), NuVasive, Inc., 2005, 2 pages.
CoRoentTM XL & XLR Marketing Brochure (9004225 A.0), NuVasive, Inc., 2005, 2 pages.
CoRoent® XL & XLR Marketing Brochure (9004225 B.0), NuVasive, Inc., 2006, 2 pages.
CoRoent® XL & XLR Marketing Brochure (9004225 C.0), NuVasive, Inc., 2007, 2 pages.
Telamon Verte-Stack PEEK Vertebral Body Spacer Brochure, medtronic Sofamor Danek, 2003, 2 pages.
Telamon Implantation Guide, Medtronic Sofamor Danek, 2003, 10 pages.
Synthes Vertebral Spacer-PR Brochure, Synthes Spine, 2002, 2 pages.
Verte-Stack PEEK Stackable Corpectomy Device, Medtronic Sofamor Danek, 2002, 11 pages.
Synthes Vertebral Spacer—AR brochure, Synthes Spine, 2006, 4 pages.

\* cited by examiner

VERTEBRAL BODY REPLACEMENT

CROSS REFERENCE TO RELATED APPLICATIONS

This application is a continuation of U.S. patent application Ser. No. 15/635,087, filed Jun. 27, 2017, which is a continuation of U.S. patent application Ser. No. 14/177,100, filed Feb. 10, 2014, now U.S. Pat. No. 9,687,357, which is a continuation of PCT/US2012/050218, filed Aug. 9, 2012, now expired, which claims the benefit of the filing date of U.S. Provisional Application No. 61/521,704, which was filed on Aug. 9, 2011. U.S. patent application Ser. No. 14/177,100, filed Feb. 10, 2014, now U.S. Pat. No. 9,687,357 is also a Continuation-in-Part application of U.S. patent application Ser. No. 12/661,206, filed on Mar. 12, 2010, which claims the benefit of priority to U.S. Provisional Application No. 61/159,792, filed Mar. 12, 2009 and U.S. Provisional Application No. 61/260,375, filed Nov. 11, 2009, the contents of which are incorporated herein entirely by reference.

FIELD

The present invention relates generally to spinal implants.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the pelvic region of the vertebral column. These fused vertebrae consist of the sacral and coccygeal region of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g. walking, talking, and breathing). Therefore, it is of great interest and concern to be able to both correct and prevent any ailments of the spine.

Trauma to the spine (e.g. car accident, sports injury) can cause fracturing of one or more vertebrae. Certain diseases affecting the spine (e.g. tumors, osteoporosis) can cause degeneration of the spine. Both trauma and degeneration may result in severe disruption to the spine. In these circumstances, the complete removal of one or more vertebrae may be required. If one or more vertebrae are removed, a replacement support system must be implanted in order to protect the spinal cord and maintain, or improve, the structure and integrity of the spine.

The present invention is directed at overcoming, or at least improving upon, the disadvantages of the prior art.

17 and the process of implanting the expandable vertebral body between a first vertebra and second vertebra.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The expandable vertebral body replacement disclosed herein boasts a variety of inventive features and components that warrant patent protection, both individually and in combination.

Figure 1:
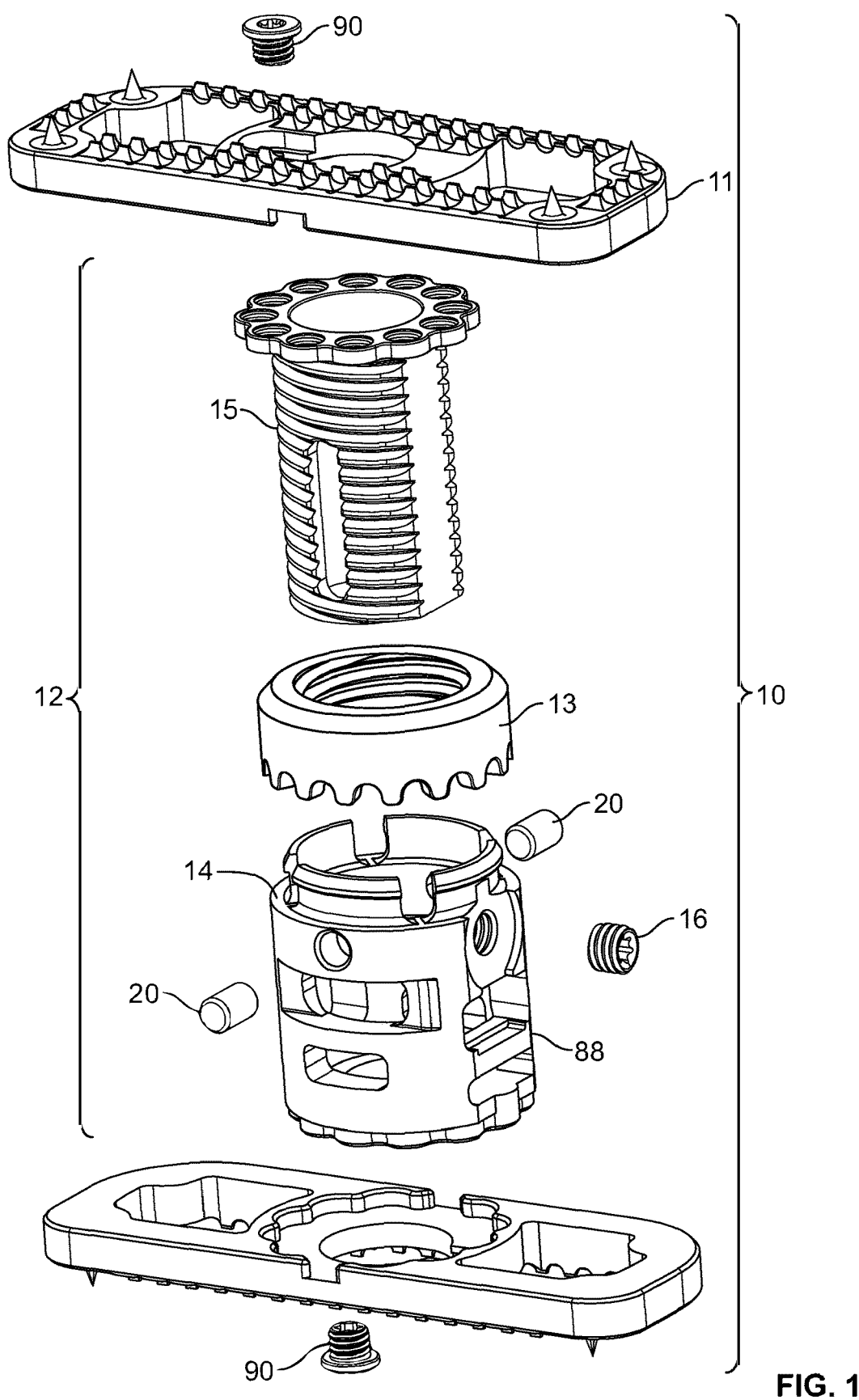
FIG. 1 is an exploded view of the vertebral body implant assembly, according to one embodiment of the present invention.

FIG. 1 illustrates an example of an expandable vertebral body replacement implant assembly 10 according to a first embodiment. The vertebral body replacement implant assembly 10 includes endplates 11 fixed at the superior and inferior ends of an expanding core body 12 wherein the expandable implant can be customized to accommodate various needs by attaching one from a selection of different endplates. The customization of the expandable core can be done in situ or moments before implantation of the expandable vertebral body replacement, which gives the benefit of customizing the implant based on expected and unexpected circumstances and conditions of the surrounding vertebral bodies.

The expanding core body 12 includes an adjustment ring 13, an outer core 14, an inner core 15, one or more guide pins 20, and one or more set screws 16. As will be explained in greater detail below, the vertebral body replacement implant assembly 10 of the present invention may be inserted into a space left by the removal of at least part of one or more vertebra in order to maintain a desired spacing between the remaining vertebrae and to stabilize the affected spinal segments. To do so, the vertebral body replacement implant assembly 10 is placed, preferably in a collapsed state, in the space between the remaining superior and inferior vertebral bodies. Rotation of the adjustment ring 13, which is fixed at one end of the outer core 14 of the core expanding body 12, results in the expansion of the core expanding body 12 due to the outer core 14 and inner core 15 moving in opposite directions along their central axis. Expansion of the core expanding body 12 may be continued until the desired spacing between the vertebral bodies is achieved. Once the desired spacing is reached, a set screw 16 in the wall of the outer core 14 is engaged into the exterior threads 31 or non-threaded area 49 of the inner core 15 to secure the expanded position of the vertebral body implant assembly 10 and prevent further height alterations of the vertebral body implant assembly 10.

Figure 2:
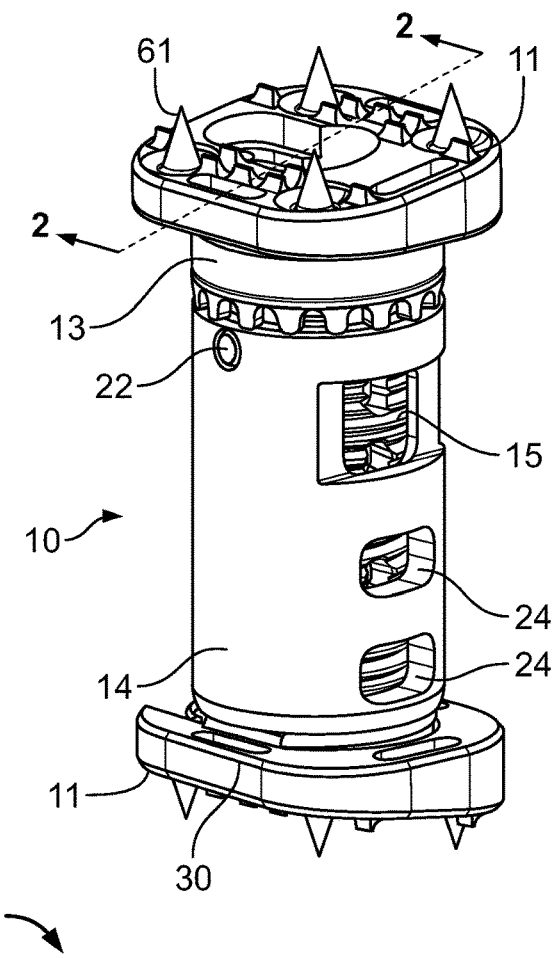
FIG. 2 is a perspective view of an alternative embodiment of the vertebral body implant assembly.
Figure 2A:
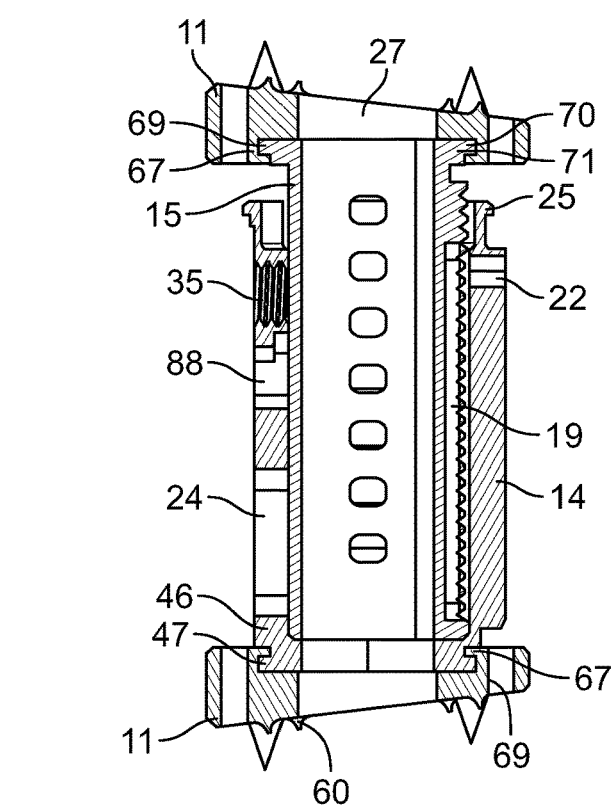
FIG. 2A is a cross section view of the vertebral body implant assembly of FIG. 2 taken along lines 2-2 of FIG. 2.
Figure 3:
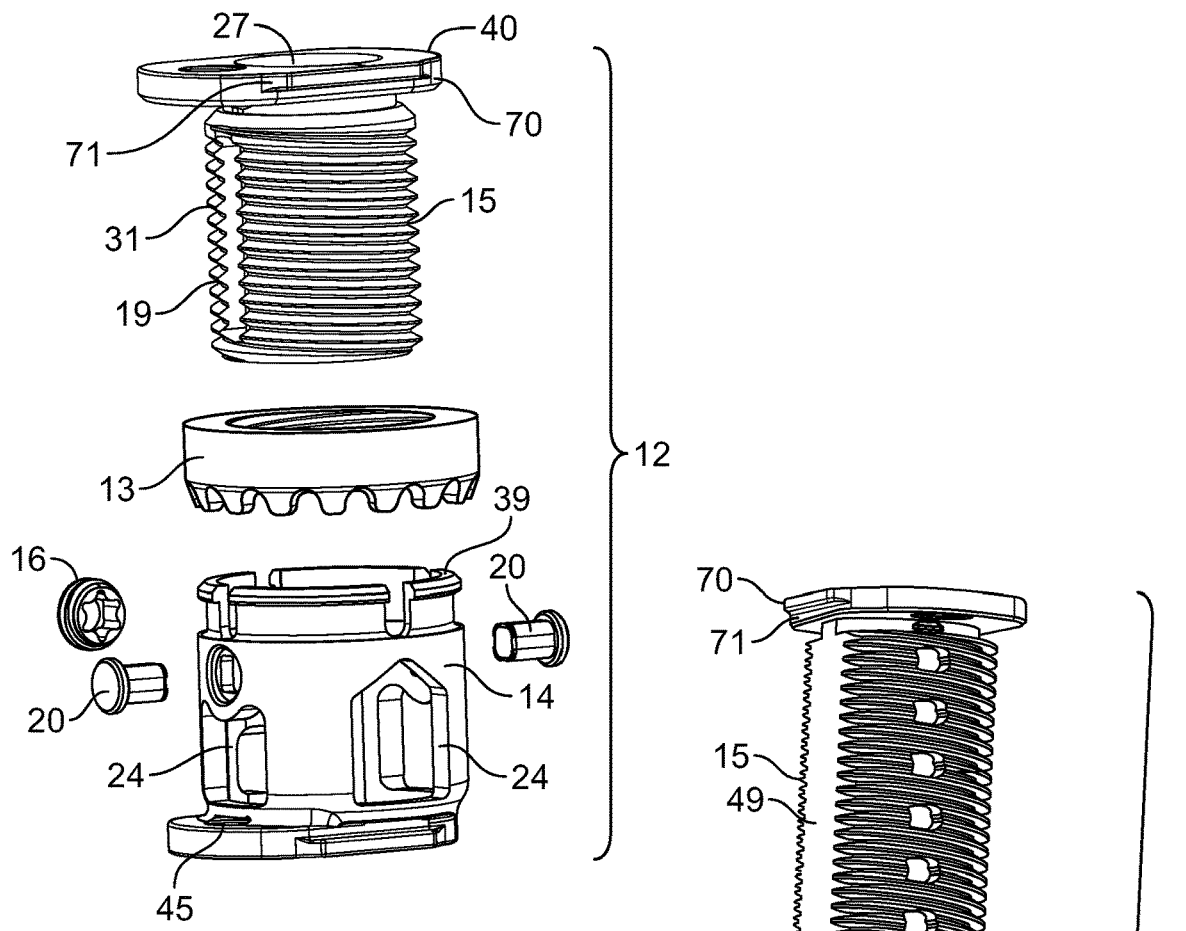
FIG. 3 is an exploded view of an alternative embodiment of the core expanding body forming part of the implant assembly of FIG. 1.
Figure 4:
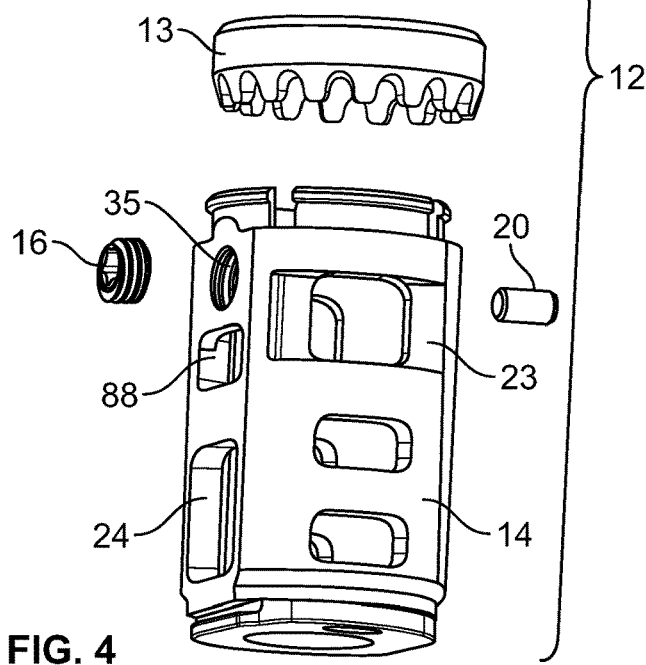
FIG. 4 is an exploded view of an alternative embodiment of the core expanding body forming part of the implant assembly of FIG. 1.

FIGS. 2 and 2A show an alternative embodiment of the vertebral body replacement implant assembly 10. FIG. 2A is a cutaway view with the adjustment ring 13 removed for greater detail of the first end 39 of the outer core 15 and the inner core 14. FIGS. 3 and 4 show exploded views of alternative embodiments of the core expanding body 12. All of the displayed configurations, shown as examples only, may be used without departing from the scope of the invention.

Referring to FIGS. 2-8, the outer core 14 includes indented slots 23, an opening 24, a first end 39, a second end 41, a plurality of flanges 25 with a distal step 26 forming a groove 44, a set screw opening 35, and a specially sized aperture 88. Indented slots 23 on the exterior wall of the outer core 14 allow for the anti-rotational attachment of the expanding tool, described below. The openings 24 in the wall of the outer core 14 allow the transport of blood and nutrients through the core expanding body 12 once implanted, which assists in new bone growth between the remaining vertebra. Larger openings 24 in the side of the outer core 14 allow the placement of additional bone growth promoting material to be added once the vertebral body implant assembly 10 has been positioned in the body and expanded to a desired height. A plurality of flanges 25 with a distal step 26 extend from the first end 39 of the outer core 14 and function to secure the attachment of the adjustment ring 13 to the first end 39.

Figure 5:
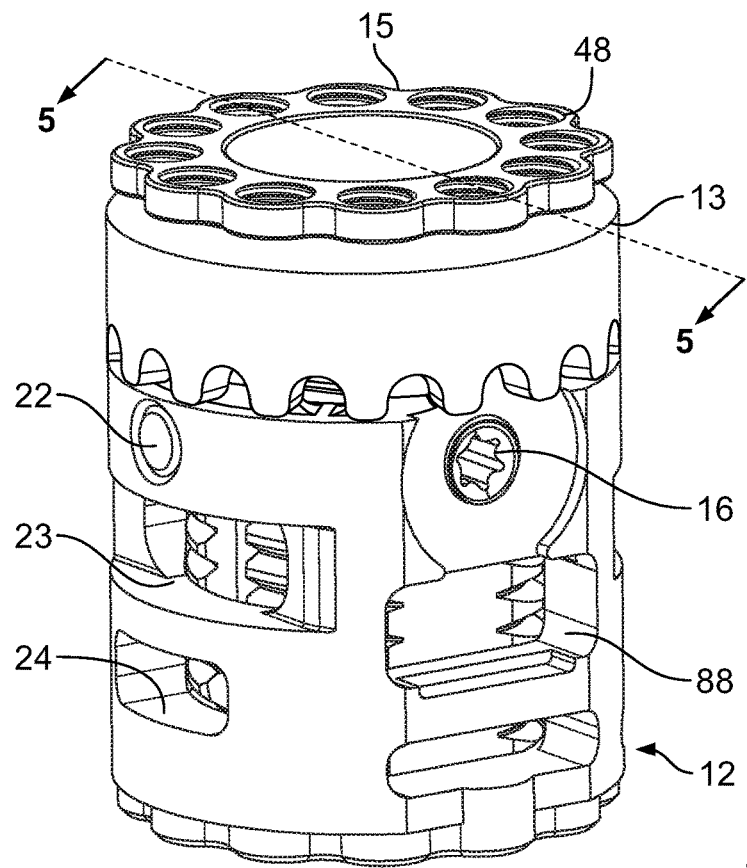
FIG. 5 is a perspective view of the core expanding body forming part of the implant assembly of FIG. 1.
Figure 5A:
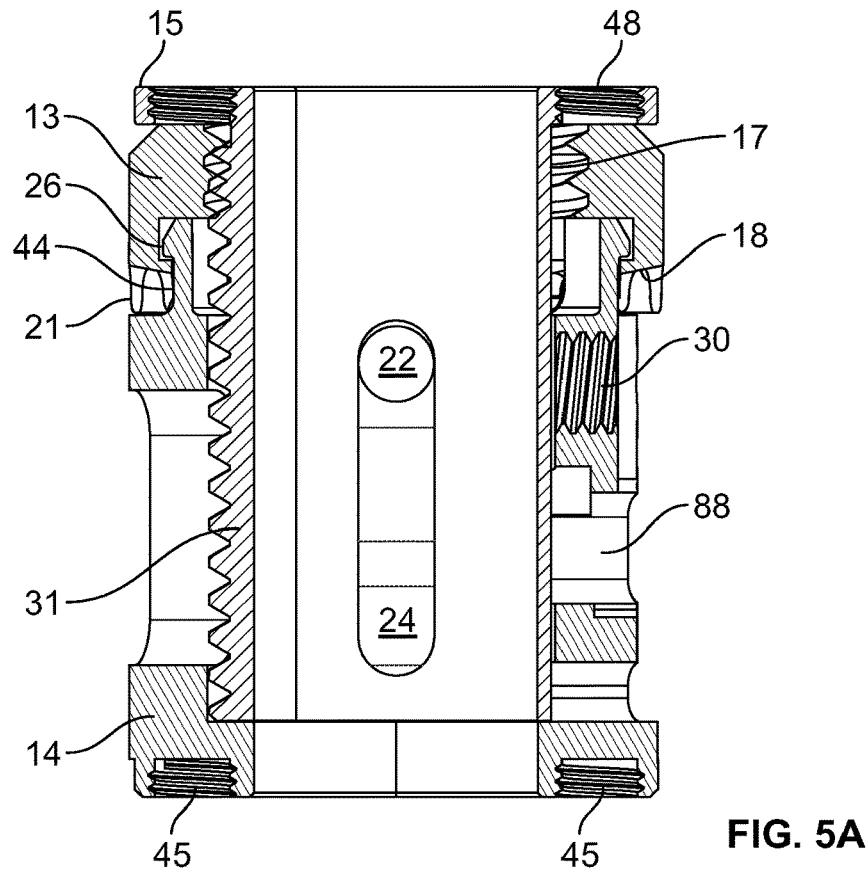
FIG. 5A is a cross section view of the core expanding body of FIG. 5 taken along lines 5-5 of FIG. 5.

As seen in FIG. 5, the outer core 14 may have a specially sized aperture 88 directly adjacent to the set screw opening 35 that allows for the insertion of the expanding tool 200, described below. The outer core 14, shown by way of examples in FIGS. 6 and 8, may include a second end slot 47 and second end groove 46 which allow similarly configured endplates 11 to slide on to the outer core 12 and hold the endplate 11 in place. The connection may be augmented through the use of a endplate attachment screw 90 placed through the endplate hole 62 and in the screw slot flange 68 through to base threaded hole 45 on the second end 41 of the outer core 14.

Figure 7:
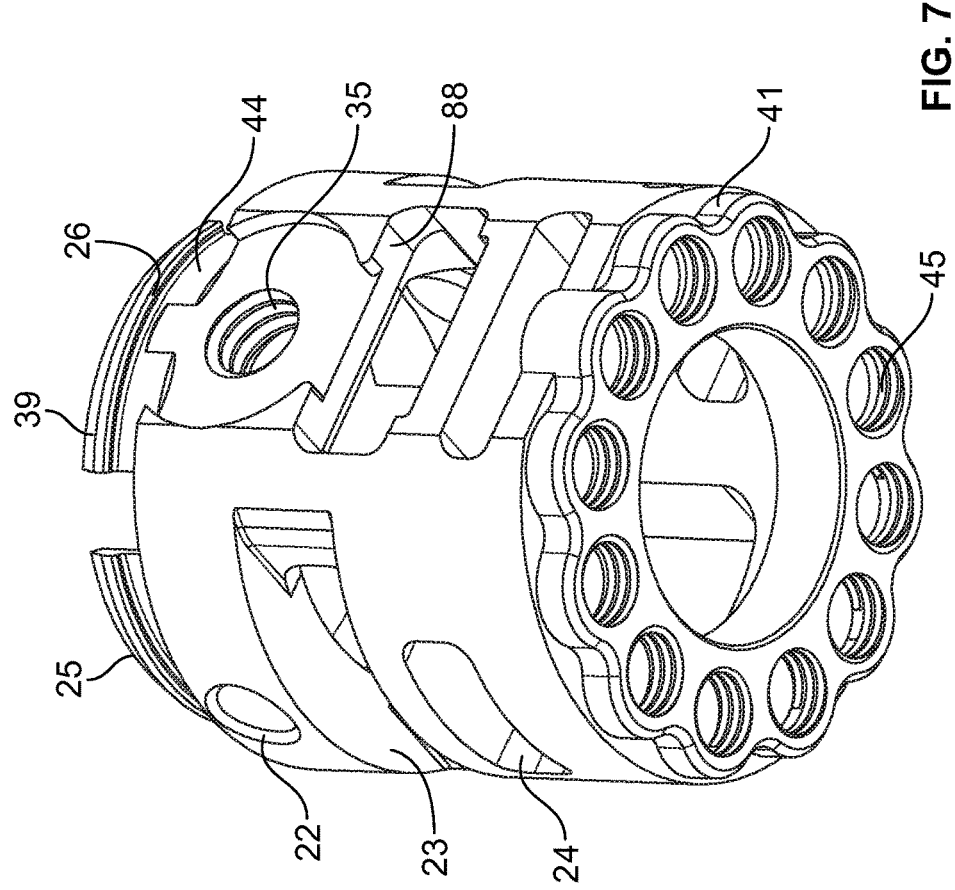
FIG. 7 is a perspective view of an alternative embodiment of the outer core forming part of the implant assembly of FIG. 1.

By way of example in the embodiment as seen in FIG. 7, the outer core 14 may have base threaded holes 45 encircling a central aperture at the second end 41 defining a generally sinusoidal or flower-shaped perimeter of the attachment portion. The base threaded holes 45 allow for an endplate 11 to be placed in different rotational positions that provides for additional customization. Though no set configuration or number of base threaded holes 45 is needed to fall within the scope of the invention, in the illustrated embodiment there are 12 threaded holes 45 to allow for attachment of the endplate 11 at 12 different angles relative to the expandable core body 12. It is contemplated that the attachment portion of the outer core and corresponding recess in the endplate 11 may be any configuration that allows for placement of the endplate 11 at one of a plurality of angles relative to the outer core 14. The inner surface of the outer core 14 is generally round with 1 or more flat sides. The flat surface contains the set screw opening 35 in which the set screw 16 is placed and tightened to assist in locking the inner core 15 in place.

The indented slots 23, best seen in FIG. 5, serve to allow secure connection between the core expanding body 12 and the expanding tool 200. The indented slots 23 are placed on the outer core 14 without disrupting the functioning of the adjustment ring 13 or the inner core 15, and may be provided in any number of suitable shapes or dimensions without departing for the scope of the invention.

The largest diameter of the outer core 14 is preferably dimensioned to be generally in the range of 12 mm to 22 mm, respectively. The height of the outer core 14 is preferably dimensioned to be generally in the range of 14 mm to 68 mm. The height of the expandable core body assembly 12 (i.e. endplates not included in the height measurement) is preferably dimensioned to be generally in the range of 15 mm to 121 mm.

Figure 6:
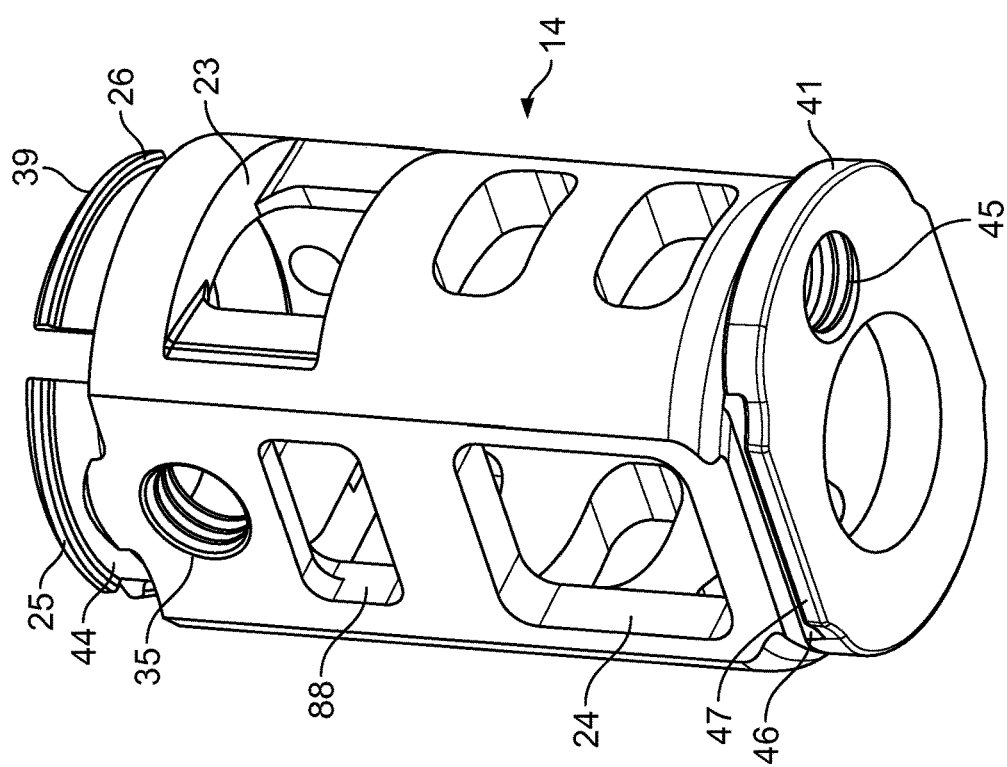
FIG. 6 is a perspective view of the outer core forming part of the implant assembly of FIG. 1.
Figure 8:
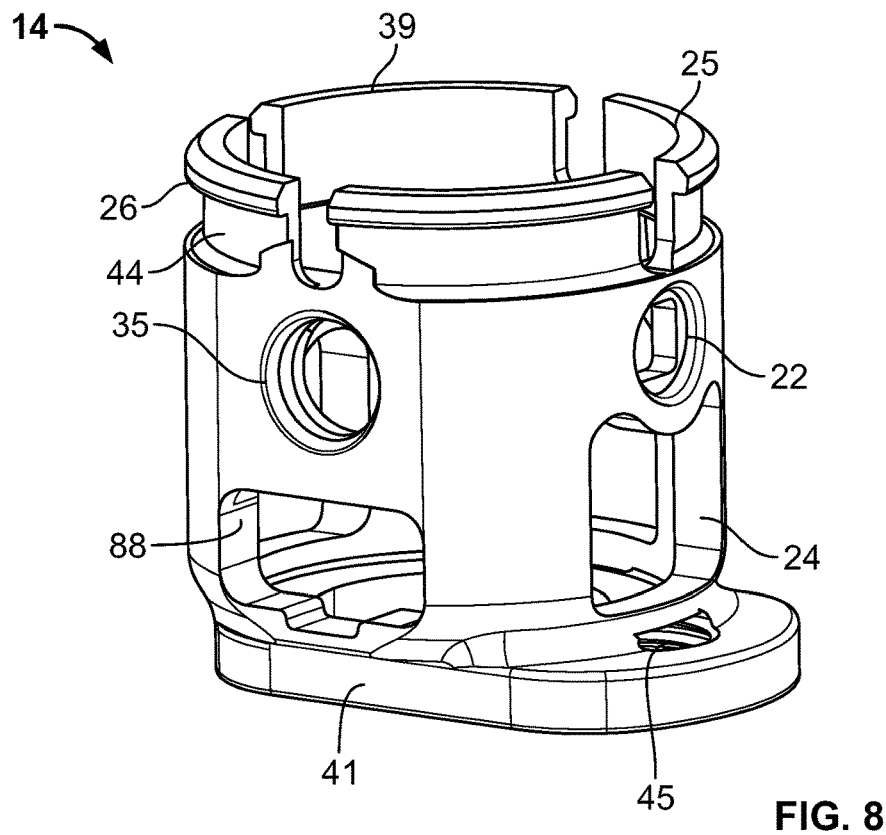
FIG. 8 is a perspective view of an alternative embodiment of the outer core forming part of the implant assembly of FIG. 1.

The adjustment ring 13, shown by way of example in FIGS. 5 and 6 includes external features 21, internal threads 17, and an annular under-step 18 forming a groove 19. When assembled, the annular under-step 18 of adjustment ring 13 engages in the groove 41 of the core expanding body 12 and the distal step 26 engages in the groove 19 of the adjustment ring 13, longitudinally fixing the adjustment ring 13 and core expanding body 12 together while permitting rotational movement therebetween. External features 21 on the adjustment ring 13 are configured to engage a combination inserter/expansion tool which may be operated to rotate adjustment ring 13 to expand core expanding body 12. The internal threads 17 of the adjustment ring 13 engage with the external threads 31 of the inner core 15 so that as the adjustment ring 13 rotates, it acts as a nut and forces the linear translation of the inner core 15 along its central axis. The longitudinal fixation of the outer core 14 to the adjustment ring 13 ensures the relative displacement of the inner core 15 to the outer core 14 as the adjustment ring 13 rotates. The diameter of the adjustment ring 13 is preferably dimensioned generally in the range of 12 mm to 22 mm. The height of the adjustment ring 13 is preferably dimensioned to be generally in the range of 5 mm to 10 mm.

Figure 9:
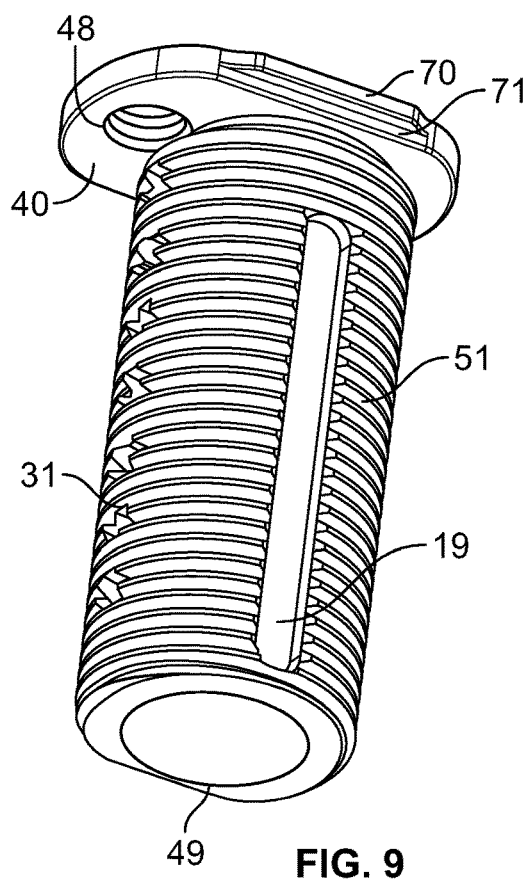
FIG. 9 is a perspective view of the inner core forming part of the implant assembly of FIG. 1.
Figure 10:
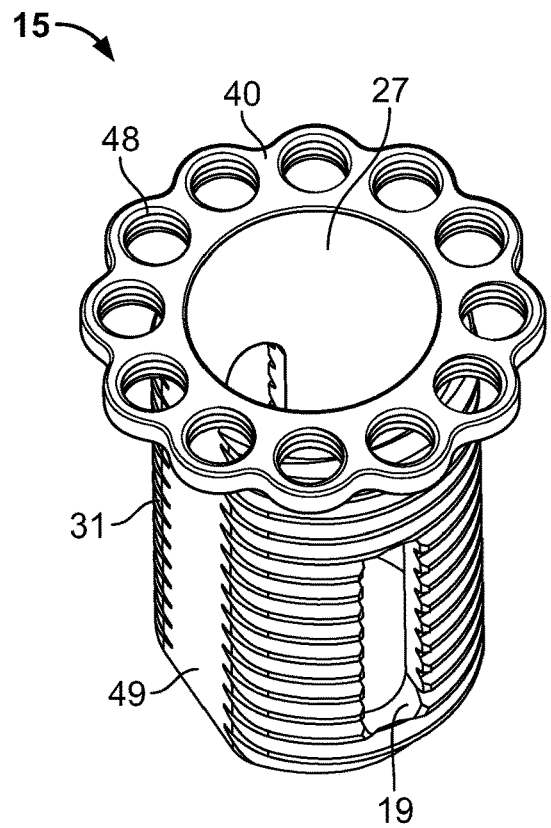
FIG. 10 is a perspective view of an alternative embodiment of the inner core forming part of the implant assembly of FIG. 1.
Figure 11:
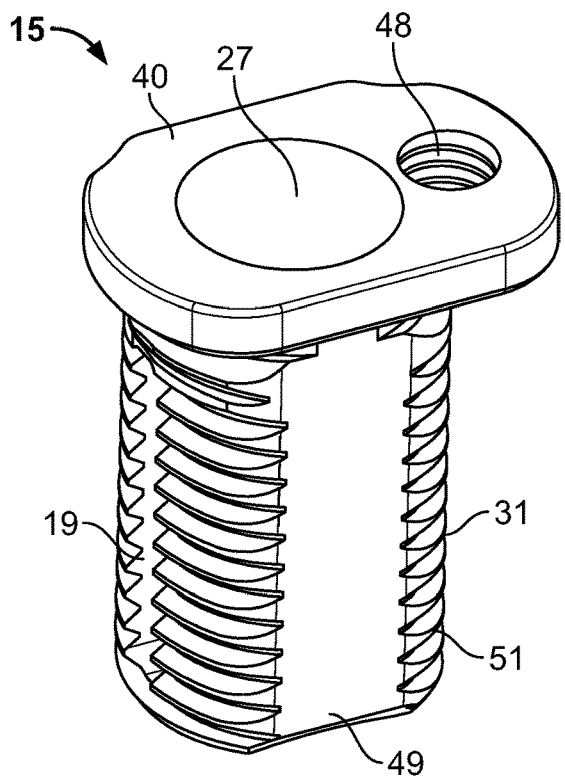
FIG. 11 is a perspective view of an alternative embodiment of the inner core forming part of the implant assembly of FIG. 1.
Figure 12:
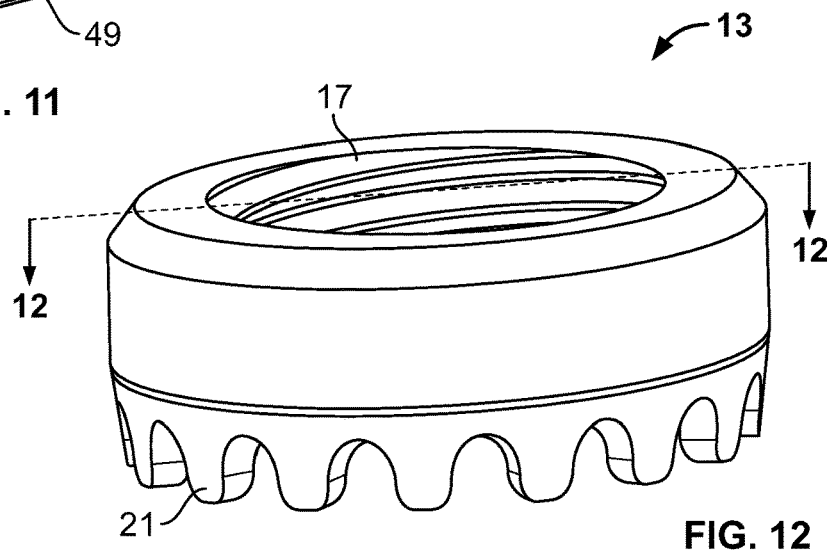
FIG. 12 is a perspective view of the adjustment ring forming part of the implant assembly of FIG. 1.
Figure 12A:
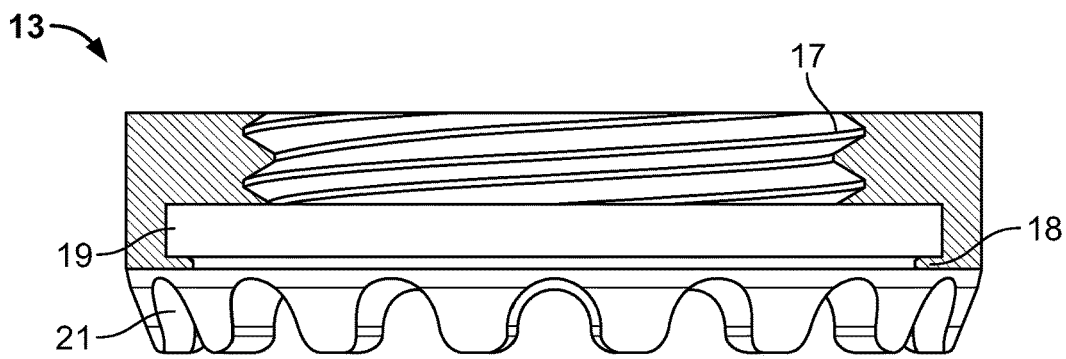
FIG. 12A is a cross section view of the adjustment ring of FIG. 12 taken along lines 12-12 of FIG. 12.

The inner core 15, illustrated in FIGS. 9-11, is composed of a first end 40 and a generally elongated body 51 extending from the first end 40, and with at least one generally helical exterior thread 31. One or more guide tracks 19 ingrained into the exterior wall of the body 51 run parallel to the central axis of the body 51. The guide track 19 receives guide pins 20 which extend through the outer core 14. A guide pin 20 travels along a guide track 19, rotationally fixing inner core 15 to outer core 14, while permitting longitudinal movement therebetween. A guide pin 20 may have threaded features that allow it to screw into threaded holes in the wall of the outer core. The rotational fixation between the inner core 15 to outer core 14 ensures that the inner core 15 and outer core 14 (and the vertebrae engaging endplates 11) remain in the desired orientation as the vertebral body implant assembly 10 is adjusted, and for the duration that it is implanted. A central lumen 27 through the inner core 15 enables additional bone growth promoting material to be placed within the expanding core body 12, and ultimately to allow new bone to form uninterrupted through the entire central axis of the vertebral body replacement implant assembly 10. The central lumen 27 may be generally cylindrical in shape (having a generally circular cross-section) or in the alternative may have a cross section having any geometric shape without departing from the scope of the present invention.

The inner core 15 may also contain a flat, non-threaded area 49 running some distance vertically along the outer surface. The non-threaded area 49 is designed to fit next to the inner flat surface of the outer core 14. The inner core 15 can be locked in place via the friction created when the set screw 16 is tightened into the non-threaded area 49.

The first end 40 of the inner core 15 may have a number of different configurations in which attachment to the endplate 11 is possible. As shown in FIG. 10, the first end 40 may consist of encircling threaded holes 48—with the same features as described above for the exemplary configuration of second end 41 on the outer core 14. The threaded holes 48 allow for secure attachment through the use of an endplate attachment screw 90 to attach the inner core 15 to the endplate 11 configured to accept a screw. This arrangement allows for rotational customization of the endplate prior to insertion into the patient.

Figure 15:
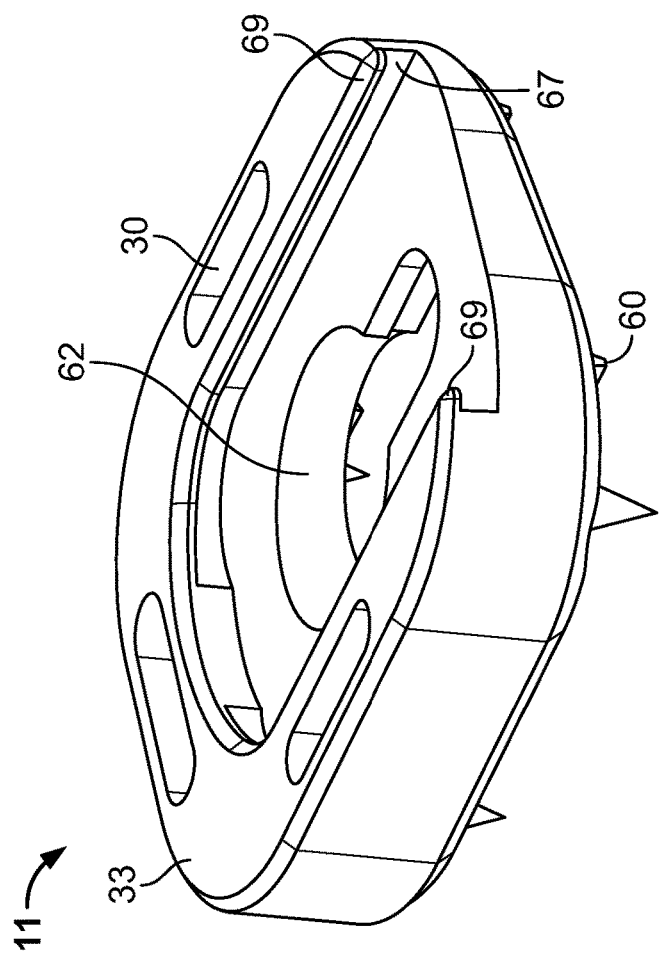
FIG. 15 is a perspective view of the bottom of the endplate of FIG. 13.
Figure 17:
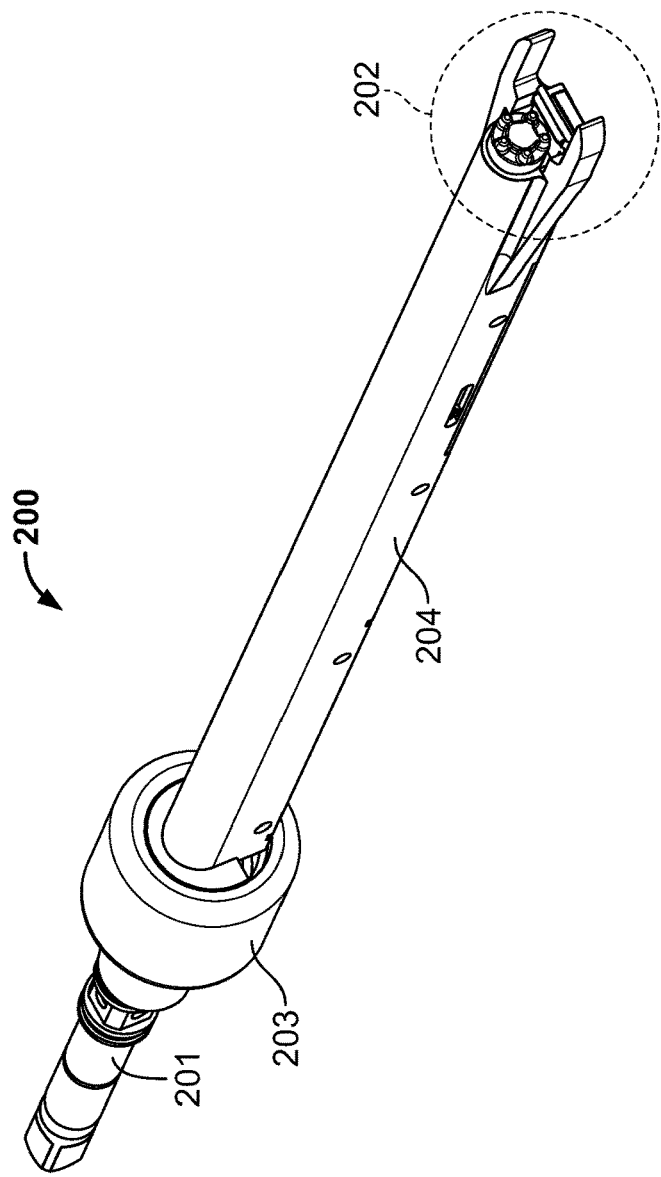
FIG. 17 is a perspective view of one example of a combined insertion and expansion, according to one embodiment of the present invention.
Figure 18:
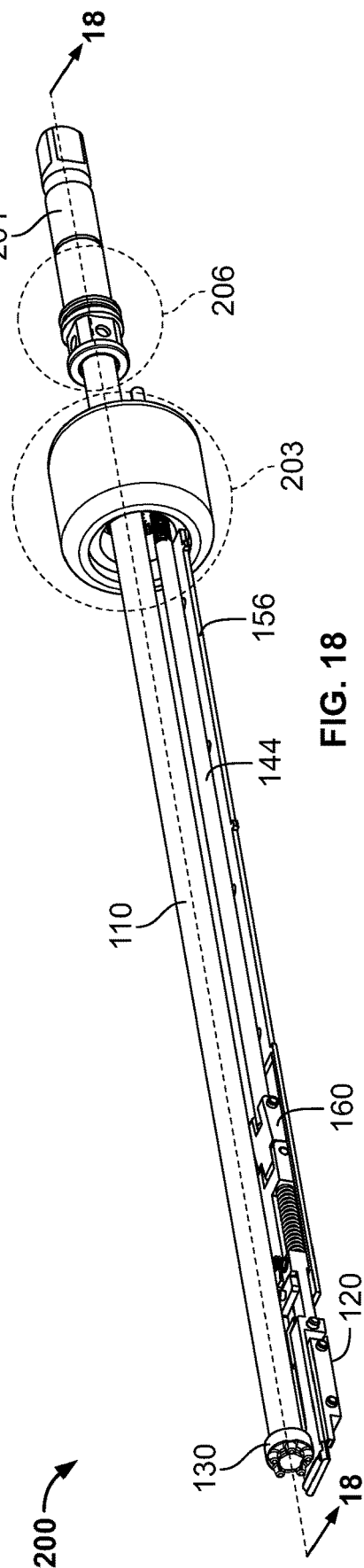
FIG. 18 is a perspective view of the expanding tool of FIG. 17 with the outer cover removed.

An alternative embodiment for the first end 40 of the inner core 15 includes a side flange 70 and groove 71 best seen in FIG. 9. The side flanges 70 and groove 71 are specifically designed to fit with a variation of endplate 11 (as shown, for example, in FIG. 15) with matching endplate flanges 69 and endplate grooves 67 by sliding the endplate 11 along the surface of the first end 40 so the flanges on each piece rest within the grooves of the other. While shown in FIG. 15 with the attachment feature of the endplate 11 configured for insertion of the engagement feature on the inner core 15 parallel to the longitudinal axis of the endplate, it is also contemplated that the attachment feature of the endplate may be configured for insertion of the inner core at an angle oblique to the longitudinal axis. Both the first end 40 and the endplate 11 may contain a hole for the insertion of an endplate attachment screw 90 to lock the endplate 11 in place. This screw connection feature may be accomplished in similar ways without departing from the scope of the patent. The perimeter shape of the first end 40 may be provided in any number of suitable shapes or dimensions without departing from the scope of the invention, provided that the perimeter shape corresponds to the perimeter shape of the attachment features of the endplate 11.

The endplate attachment features discussed above allow for the unique ability to customize the core expanding body 12 with various endplate 11 configurations. The ability to customize the core expanding body 12 may provide numerous advantages. By way of example, the customizable core expanding body 12 can be used in a variety of surgical approaches (e.g. anterior, anterior-lateral, lateral, posterior or posterior-lateral). By way of further example, the customizable core expanding body 12 can be placed in a variety of positions along the spine, and the customizable core expanding body 12 can be made compatible with a variety of conditions of the surrounding vertebral bodies (e.g. partial removal of vertebral body).

The vertebral body implant assembly 10 is preferably composed of either metal (e.g. titanium, stainless steel, etc.) or polymer (e.g. poly-ether-ether-ketone (PEEK)). When the implant assembly is made out of a polymer, one or more marker rods 61 are preferably composed of a radiopaque material (e.g. titanium) and are positioned within the vertebral body implant assembly 10 so that the positioning of the vertebral body implant assembly 10 can be visible upon X-ray imaging. This visual indication may be obtained either post-operatively or intra-operatively to confirm placement of the vertebral body implant assembly 10. Additionally, in patients where one or more vertebral bodies have been removed due to diseases, such as tumors, and an vertebral body implant assembly 10 has been implanted between the remaining vertebral bodies, it is beneficial during post-operative x-ray imaging to be able to see through the implant in order to detect any reoccurrence of the disease.

Figure 13:
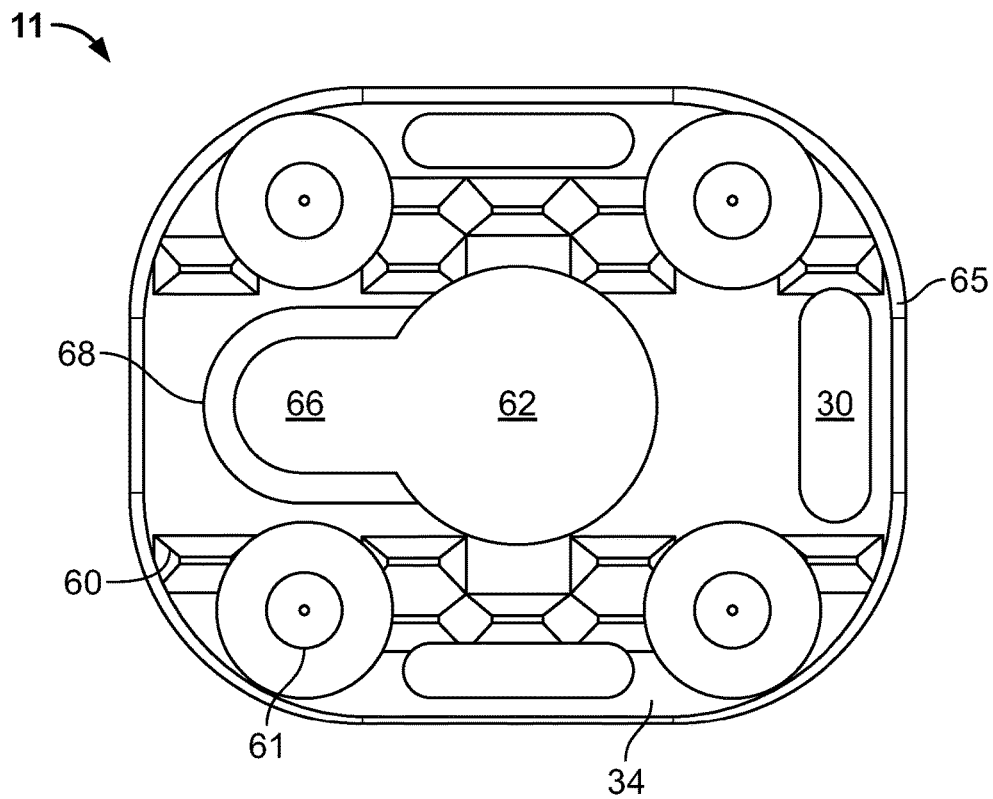
FIG. 13 is a top view of the endplate forming part of the implant assembly of FIG. 1.
Figure 14:
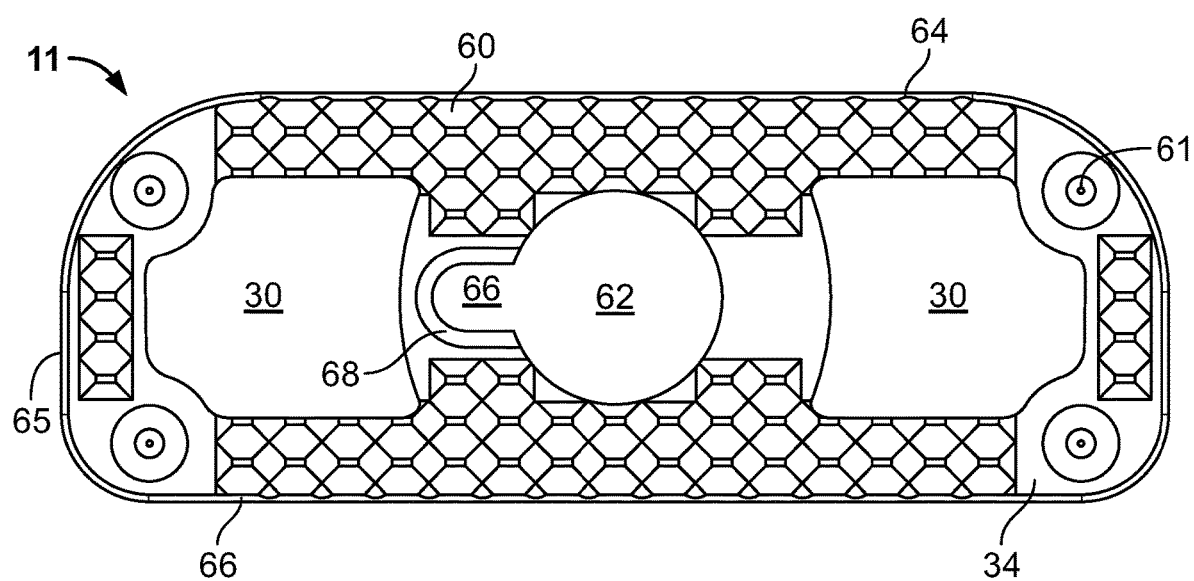
FIG. 14 is a top view of an alternative embodiment of the endplate forming part of the implant assembly of FIG. 1.

FIGS. 13-14 illustrate the second surface 34 of the endplate 11 which includes one or more liner ridges 60, the center hole 62, an anterior side 64, a posterior side 66, lateral sides 65, a screw slot 63, a screw slot flange 68, one or more windows 30, and one or more marker rods 61. When implanted, the second surface 34 is configured to be positioned against the adjacent vertebral body with the anterior side 64 positioned generally towards the anterior side of the adjacent vertebral body. The generally larger radii corners at the ends of the anterior side 64 are configured to generally conform to the natural shape of the anterior portion of a vertebral body. In the exemplary embodiment shown, for example, in FIG. 14, the endplate 11 is configured for a preferred use through a lateral approach to the spine, and preferably when endplate coverage is desired to span across the ring apophysis of the vertebra. The distance between the two lateral sides 65 has a length dimensioned to extend generally across the space from the apophyseal ring at one lateral aspect of the spine to the apophyseal ring at the other lateral aspect of the spine. This allows the endplate 11 to provide more support and distribute the weight more evenly throughout the adjacent vertebral body, which lessens stress and potential damage to the adjacent vertebral body. The ridges 60, provide additional placement stabilization and are shown in this embodiment to be generally parallel to the lateral sides 65. The ridges 60 may also travel parallel to or in angled directions from the anterior or posterior side 64, 66, without departing from the scope of the invention. While the ridges 60 are shown as linear, it will be appreciated that the ridges 60 may be non-linear without departing from the scope of the present invention. The travel of the ridge 60 is generally along the entire length of the lateral side 65, but it may only travel a portion of the lateral side 65, or any side, without departing from the scope of the invention, and therefore is not limited to the length of travel that the ridge 60 makes along the second surface 34 of the endplate 11.

The endplate attachment screw 90, best seen in FIG. 1, provides a locking mechanism for attachment of the endplate 11 to the inner core 15. As discussed above, the first end 40 of the inner core 15 and the second end 41 of the outer core 14 may consist of different configurations to attach the endplate 11 such as, by way of example, a sliding flange and groove method and a variable screw placement method. The screw slot 63 allows for the insertion of an endplate attachment screw 90 to connect the endplate 11 to the inner core 15. The endplate attachment screw 90 can hold the endplate to the inner core 15 by means of the screw slot flange 68 within the screw slot 63.

In addition to the endplates shown, there are many other shapes and sizes that can be alternative embodiments of the present invention. According to the embodiments of the present invention, it is contemplated that the endplates 11 may be generally oval or rectangular in shape (as shown in FIGS. 13-14) meaning they have a length dimension longer than a width dimension. Alternatively, the endplates 11 may be circular in shape. By way of example only, the different directions of travel of the ridges 60 on the second surface 34 cater to different spinal procedures, particularly pertaining to the direction of implant insertion. Also, an asymmetrical shape of endplate 11 is possible. This type of endplate is configured for a preferred use through a lateral approach, and generally under the circumstance where a partial removal of the adjacent vertebral body has been performed and endplate coverage is to be biased in one direction relative to the core expanding body 12. The width of an endplate is defined as the distance between the anterior side and posterior side of an endplate. Therefore, in one particular embodiment, the width of endplate 11 is preferably dimensioned generally in the range of 12-22 mm. The length of an endplate is defined as the distance between the opposing lateral sides of an endplate. Therefore, in one particular embodiment, the length of endplate 11 is preferably dimensioned generally in the range of 15-60 mm. The variable lengths of the sides of endplate 11 make the core expanding body 12 even more customizable and enable the vertebral body replacement implant assembly 10 to maximize the surface area contact between the endplates 11 and the adjacent vertebral body, resulting in the ability to provide the most stable support.

Figure 16:
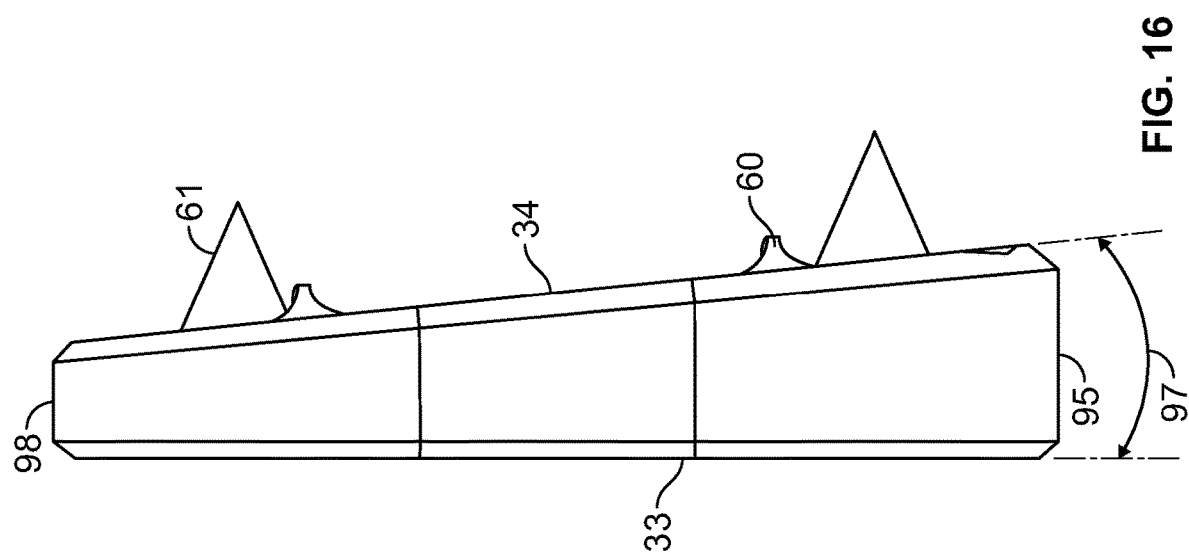
FIG. 16 is a side view of the endplate of FIG. 13.

The endplate 11 may also have a variety of shapes of the first and or second surfaces. For example, second surface 34 may be generally planar or the second surface 34 may be convexly curved to complement the contoured surface of a vertebral body endplate. According to another embodiment, the endplate 11 may be provided with one of a variety of angles between the first surface 33 and second surface 34 of endplate 11. FIG. 16 demonstrates an exemplary embodiment of an angled endplate 94. The angle 97 that will be described for endplate 94 is available in any of the previously described endplates and is therefore not limited to only endplate 94. By way of example only, the angle 97 of the endplate 94 is preferably dimensioned generally in the range of −4-15 degrees and functions to improve the natural curvature of the spine when implanted. The preferred direction of the angle 97 formed between the first surface 33 and second surface 34 lies generally in a plane that is either along or parallel to a ridge 60, which in this example also happens to be parallel to the lateral sides 96. This configuration is intended to accompany specific procedures and directions that the endplate 94 will be implanted relative to adjacent vertebral bodies. Additionally, the angle 97 that is formed between the first surface 33 and second surface 34 may benefit the maintenance or correction of, for example, either the lordotic or kyphotic curvature of the spine, depending on the direction of angulation. By way of example only, if the distance between the first surface 33 and second surface 34 is greater at the anterior side 95 than the posterior side 98 of the endplate 94, then it can be assumed that the endplate 94 is configured to have the preferred use to correct or maintain lordosis.

One or more windows 30 provide for the insertion of bone growth material, blood and nutrient access throughout the area, and new bone growth to form around the implant. Windows 30 can be of various shapes and sizes, and placed in different configurations on the second surface 34 in conjunction with the ridges 60 without departing from the scope of the present invention. At least one marker rod 61 is press fit into the second side 34 of the endplate 11. The shape of the marker rod 61 is generally conical. The formation of the marker rods 61 are shown by example to be positioned in a rectangular formation, but can be positioned in other configurations without departing from the scope of the present invention.

Although described with respect to specific examples of the different embodiments, any feature of the endplates disclosed herein by way of example only may be applied to any of the embodiments without departing from the scope of the present invention. Furthermore, procedures described, for example only, involving specific regions of the spine (e.g. thoracic and lumbar) may be applied to another region of the spine without departing from the scope of the present invention and dimensioning of the implant may be adjusted to accommodate any region.

FIGS. 17-27 illustrate examples of an expanding tool 200 for use with the vertebral body replacement implant assembly 10 described above. By way of example only, the expanding tool 200 includes distal handle 201, outer cover 204, a proximal engagement region 202, adjustment region 203, and an elongated first shaft 144. The proximal engagement region 202, best viewed in FIG. 23, includes a plurality of engagement arms 166, pusher arm 120 with pusher arm tip 161, locking pins 127, pushing spacer 160, extension piece 117 with engagement lip 118, one or more springs 125, slot pins 121, blocker bar 126, outer cover slots 122, and lower cover 156. The adjustment region 203 includes large bezel 140, stopper rings 141, one or more holding rings 142, and a spur gear 142.

Figure 22:
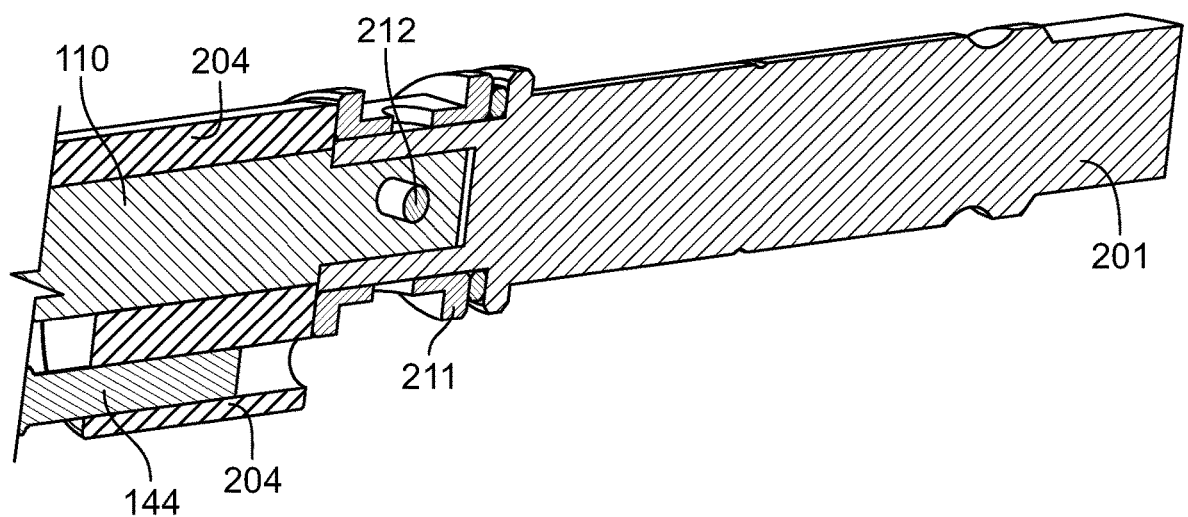
FIG. 22 is a cross section view of the distal handle taken along line 18-18 of FIG. 18.

The outer cover 204 has a number of features that allow it to securely interface with vertebral body implant assembly 10, and specifically, the outer core 14. The outer cover 204 consists of engagement arms 116 that are sized and dimensioned to securely slide into the indented slots 23 and secure the anti-rotation of the vertebral body implant assembly 10. The fitting block 119 is sized and dimensioned to fit securely within the specially sized hole 88 in the outer core 14. As best seen in FIG. 22, the distal handle 201 is connected to the elongated first shaft 110 such that the elongated first shaft 110 will rotate in conjunction with the rotation of the distal handle 201 due to the sleeve 211 and securing pin 212. The outer cover 204 is connected to the distal handle 201 by the holding ring 142 that allows for the outer cover 204 to remain non-rotational. The second shaft 144 will also not rotate with the rotation of the distal handle because the second shaft 144 is connected to the outer cover 204 (best seen in FIGS. 19 and 22).

Figure 19:
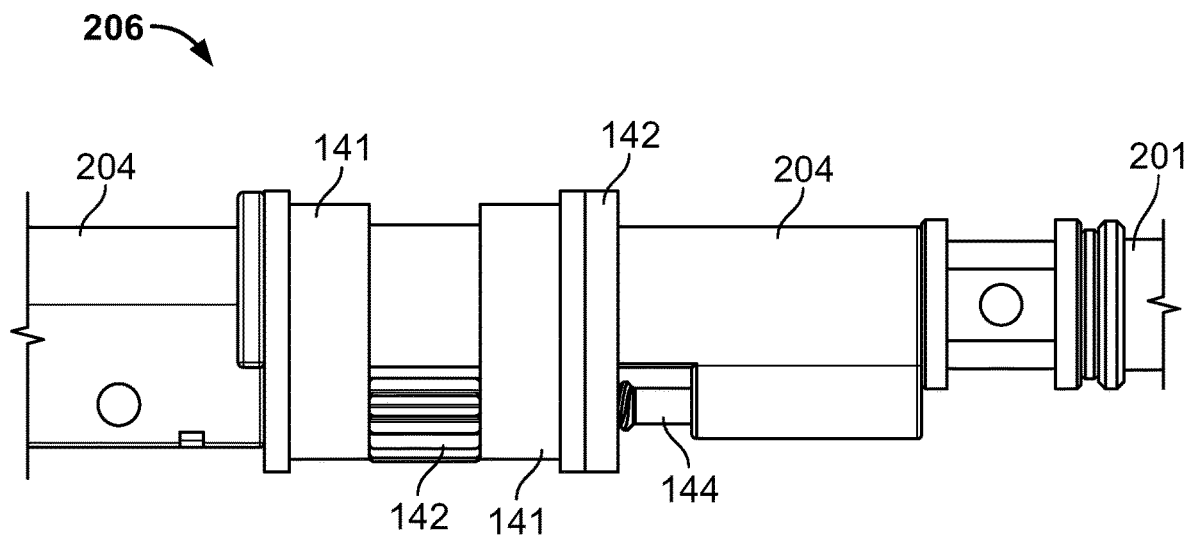
FIG. 19 is a side view of the adjustment region of the expanding tool of FIG. 17.
Figure 20:
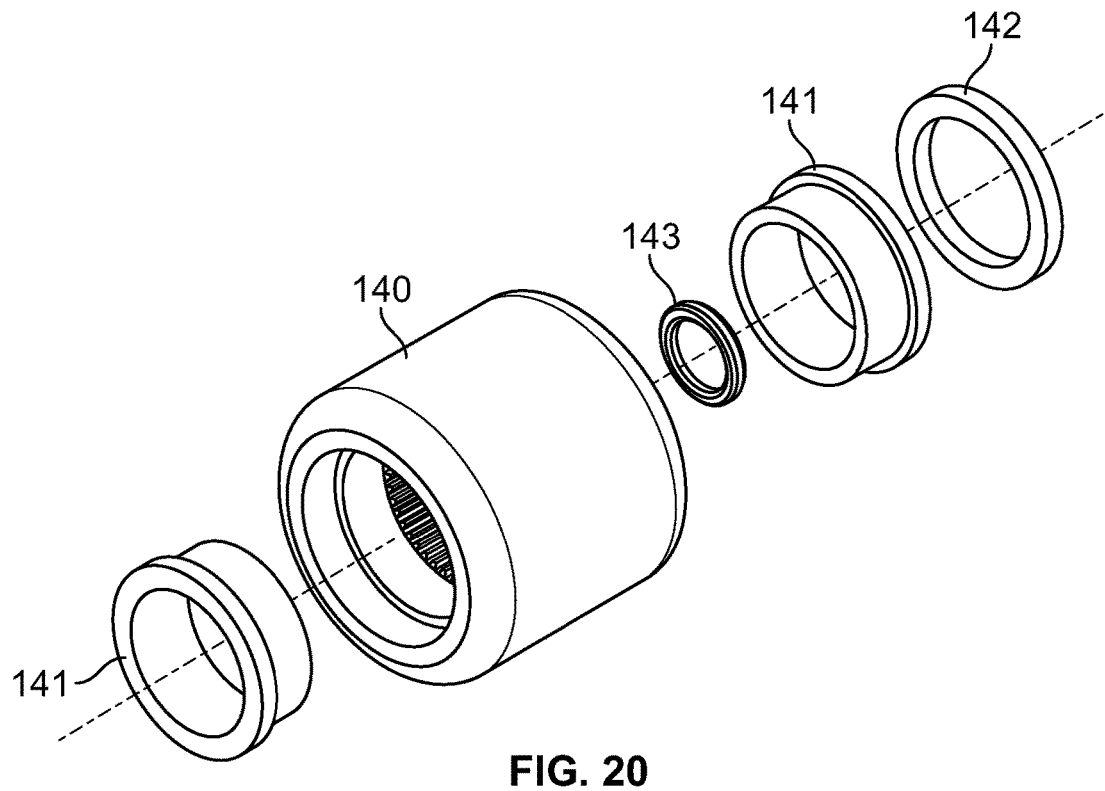
FIG. 20 is an exploded view of the large bezel forming part of the expanding tool of FIG. 17.
Figure 21:
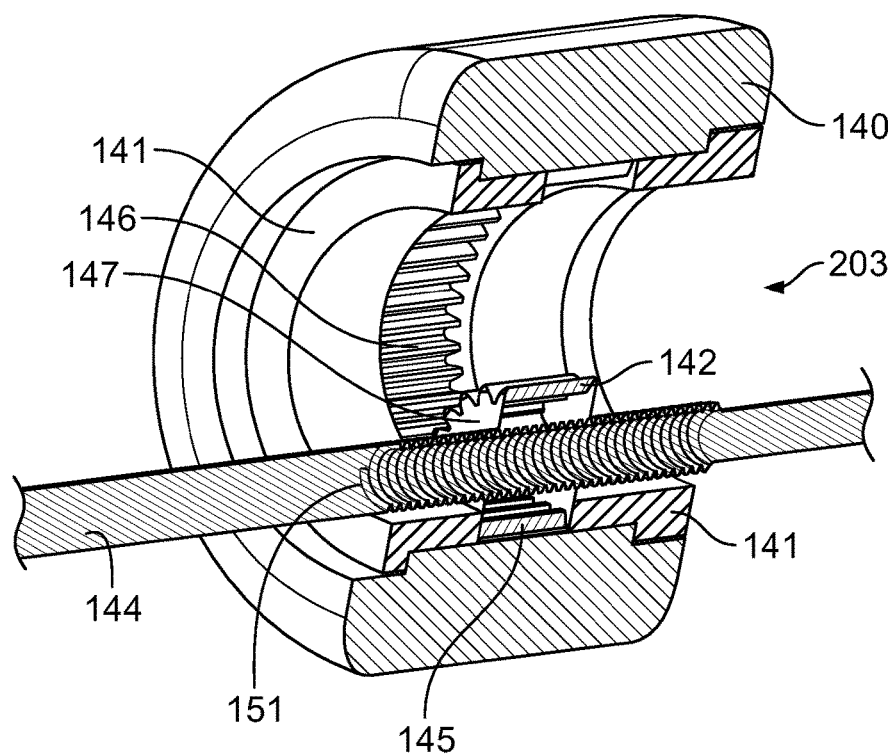
FIG. 21 is a cross section view of adjustment region taken along line 18-18 of FIG. 18.

The large bezel 140, best seen in FIGS. 19-21, is held in place by one or more stopping rings 141 and one or more holding rings 142. A geared track 145 with teeth features 146 is inside of the large bezel 140 in which the spur gear 142 sits. The spur gear teeth 147 interact with the teeth features 146 on the geared track 145 so that when the large bezel 140 is rotated, the spur gear rotates in the opposite direction. Inner threads on the inside of the spur gear 142 match the threaded features 151 on the second shaft 144. As the spur gear 142 rotates via the rotation of the large bezel 140, the inner threads interact with the threaded features 151 to transfer the rotational motion to axially motion and push the second shaft 144 horizontally parallel to the outer cover 204. The spur gear 142 is kept in place by the stopper rings 141. The second shaft 144 is held in place by the outer cover 204 and the lower cover 156. FIG. 21 shows adjustment region 203 with the large bezel 140 so that the inner workings can be appreciated.

Figure 23:
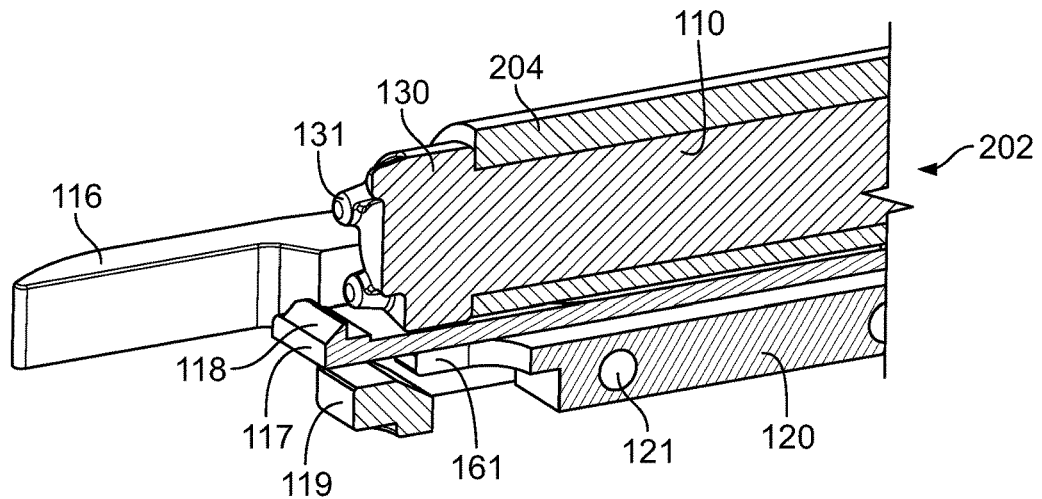
FIG. 23 is a cross section view of the proximal engagement region taken along line 18-18 of FIG. 18.
Figure 24:
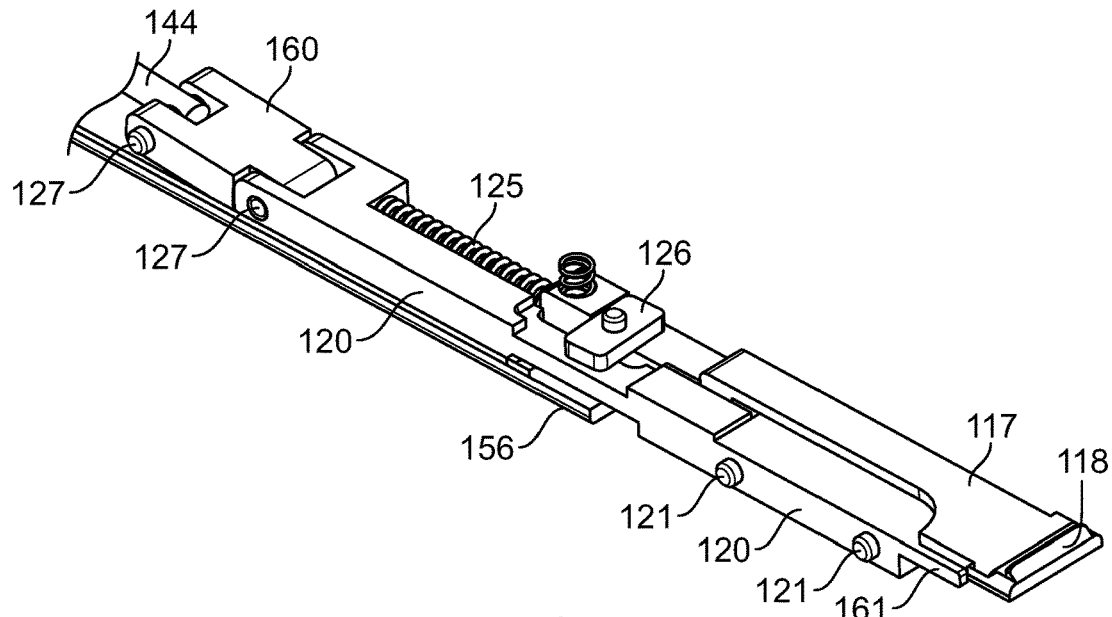
FIG. 24 is a perspective view of the proximal engagement region with the outer cover and elongated first shaft removed.
Figure 25:
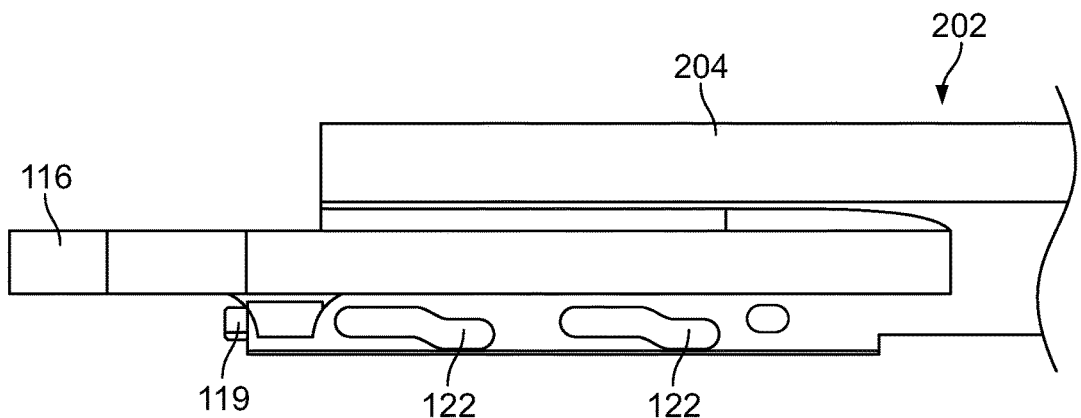
FIG. 25 is a side view of the outer cover forming part of the expanding tool of FIG. 17.

As show in FIG. 23, the chief mechanisms for interface with the vertebral body implant assembly 10 are in the proximal engagement region 202. The second shaft 144 is connected to the pushing spacer 160 by a locking pin 127. The pushing spacer 160 is connected to the pusher arm 120 by another locking pin 127 that allows for horizontal movement of the pusher arm 120 when the pushing spacer 160 is moved closer to the engagement arms 116. The spring 125 flexes so that the extension piece 117 will not move with the pusher arm 120. The blocker bar 126 prevents the pusher arm 120 and extension piece 117 from moving vertically. As the pusher arm 120 moves, the slot pins 121, specially designed to fit within the outer cover slots 122 (best seen in FIG. 25), force the pusher arm 120 vertically upward because the slot pins 121 are traveling a prescribed path set by the outer cover slots 122. The pusher arm tip 161, at the end of the pusher arm, acts on the extension piece 117 forcing it upward.

The extension piece 117 can be engaged when the outer cover 204 is in place with the engagement arms 116 securely in the indented slots 23 and the fitting block 119 resting in the specially sized hole 88. As described above, the rotation of the large bezel 140 pushes the extension piece 117 vertically upward where it can lock into the inside of the outer core 14 by the engagement lip 118. The engagement lip 118 ensures the outer core 14 will not move away from the expanding tool 200 when the expanding tool 200 is pushed up against the outer core 14 in order to rotate the adjustment ring 13. The shaft end 130 sits inside the set screw opening 35 when the expanding tool 200 is properly connected to the vertebral body assembly 10. The shaft end 130 includes adjustment features 131 that are sized and dimensioned to interact with external features 21 of the adjustment ring 13. The rotation of the distal handle 201 simultaneously rotates the elongated first shaft 110 and the shaft end 130 whereby the adjustment features 131 interact with the external features 21 so that the adjustment ring 13 rotates increasing or decreasing the distance between the endplates 11.

Figure 26:
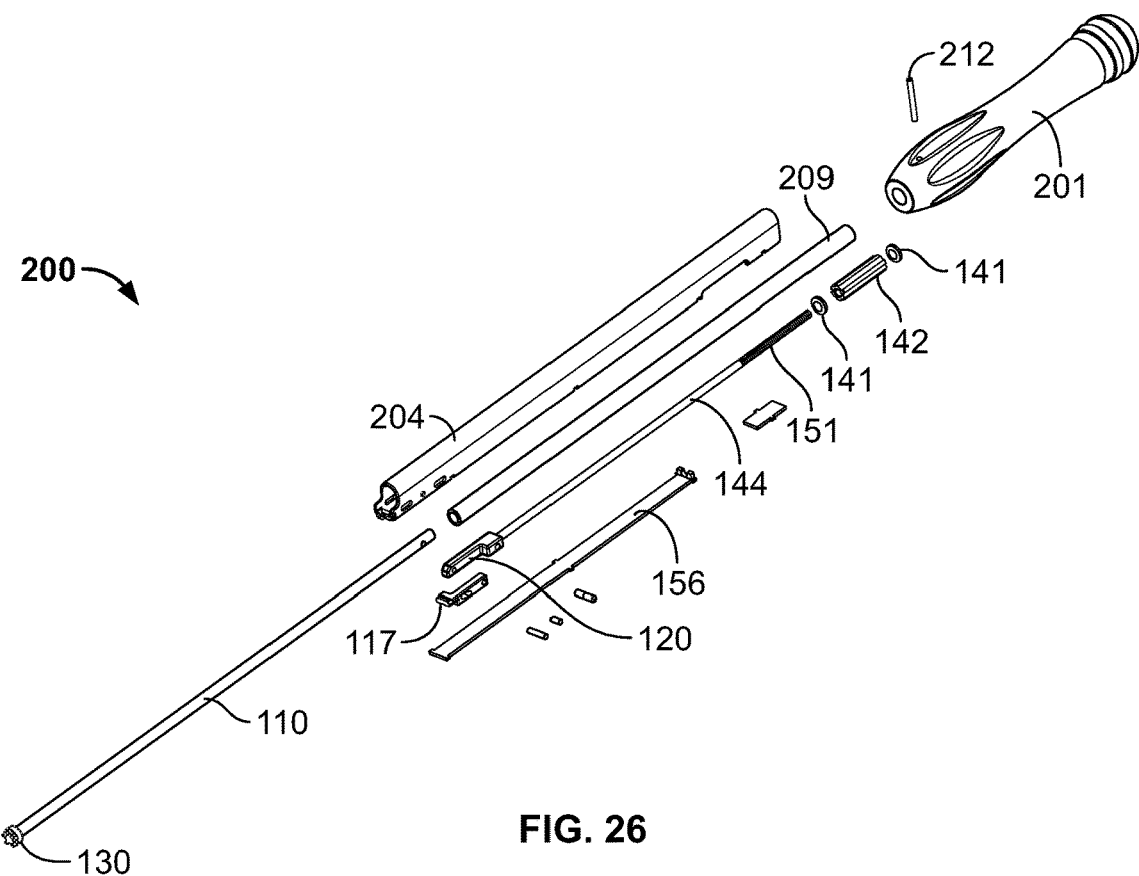
FIG. 26 is an exploded view of an alternative embodiment of the expanding tool.
Figure 27:
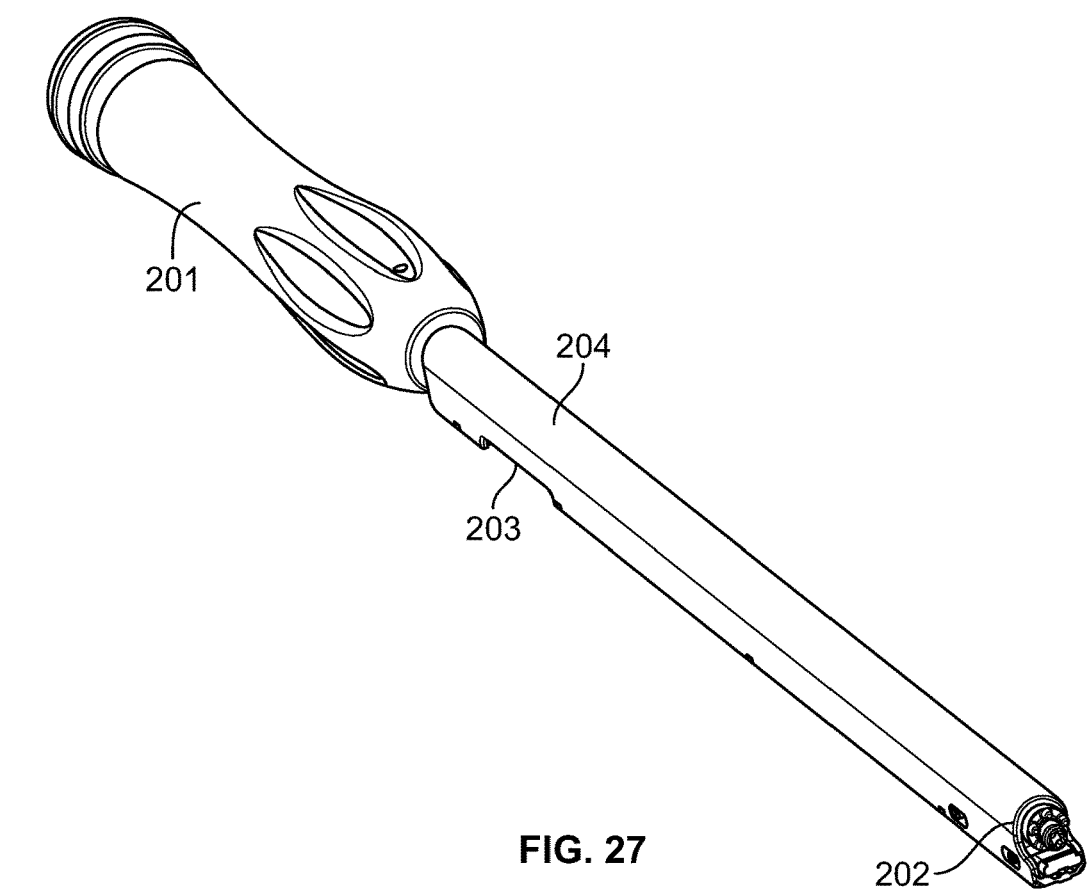
FIG. 27 is a perspective view of the expanding tool of FIG. 26.

FIGS. 26 and 27 show an alternative embodiment of the expanding tool 200. The expanding tool 200 consists of a distal handle, outer cover 204, elongated first shaft 110, first shaft cover 209, second shaft 144, lover case cover 156, rotational gear 149, stopper rings 141, extension piece 117, and pusher arm 120. The outer cover 204 includes a similar embodiment of the fitting block 119, discussed above, whereupon the fitting block 119 fits securely in the specially sized hole 88. The shaft end 130 of the elongated first shaft 110 rests in the set screw opening 35. When the distal handle 201 is rotated, the adjustment features 131 engage with the external features 21 of the adjustment ring 13. The adjustment ring 13 then rotates changing the distance between the endplates 11. This embodiment of the expanding tool 200 contains no mechanism to secure the vertebral body implant assembly 10 to the expanding tool 200.

Figure 28A:
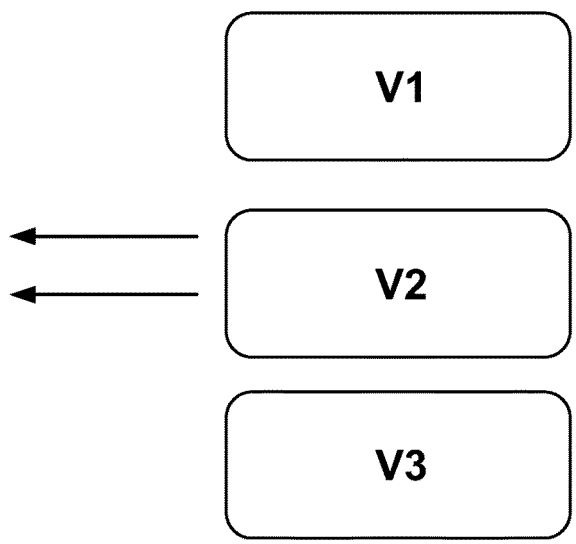
FIG. 28A-28D is a series of side views of the implant assembly of FIG. 1 engaged with the expanding tool of FIG.
Figure 28B:
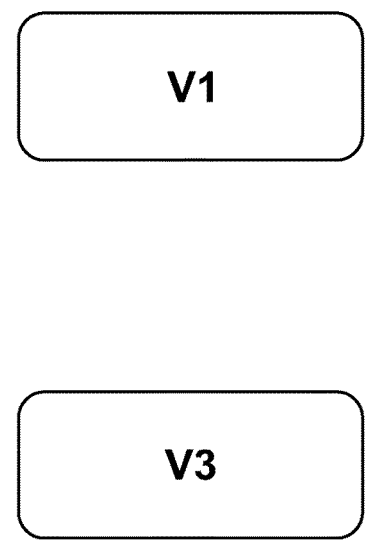

FIGS. 28A-28D illustrates one example of a preferred use of a vertebral body implant assembly 10 and the expanding tool 200. FIG. 28A shows an anterior view of a portion of a spine, which includes a superior vertebra, a medial vertebra and an inferior vertebra which are shown labeled as V1, V2, and V3 respectively. In FIG. 28B, the medial vertebra has been removed so that there is now a large space between the superior and inferior vertebral bodies. In the following figure, FIG. 28C, endplates 11 have been chosen that are preferred for being positioned against the surfaces of the superior and inferior vertebral bodies. These selected endplates 11 are shown being attached to the inner core 15 and outer core 14 of the core expanding body 12. The expanding tool 200 can then interface with the indented slots 23 of the outer core 14 by turning the distal handle 201. Once the core expanding body 12 is positioned between the engagement arms 116 and the shaft end 130 is in the set screw opening 35, the large bezel 140 is rotated to that the engagement lip 118 grasps the inside of the outer core 14 so that the core expanding body will not move when the distal handle 201 is rotated to change the axial distance between the endplates 11.

Figure 28C:
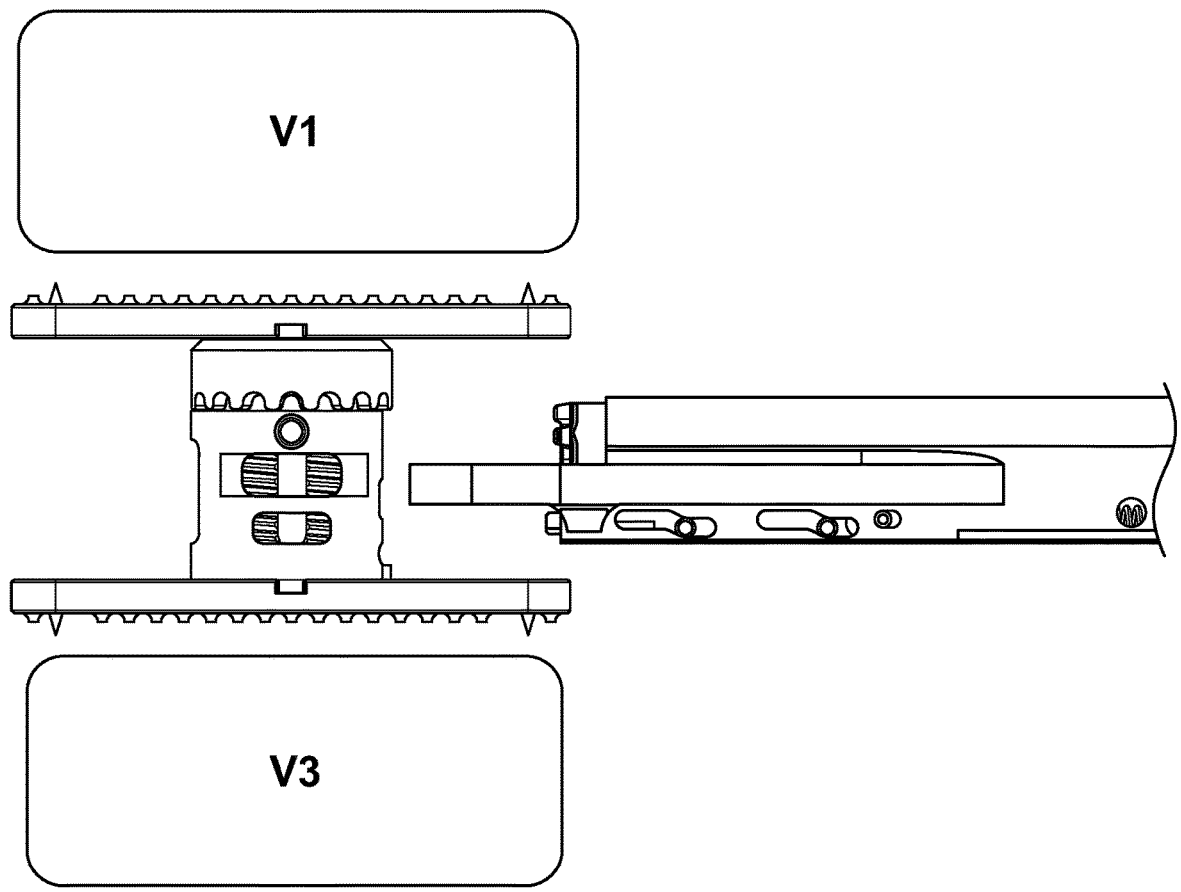
Figure 28D:
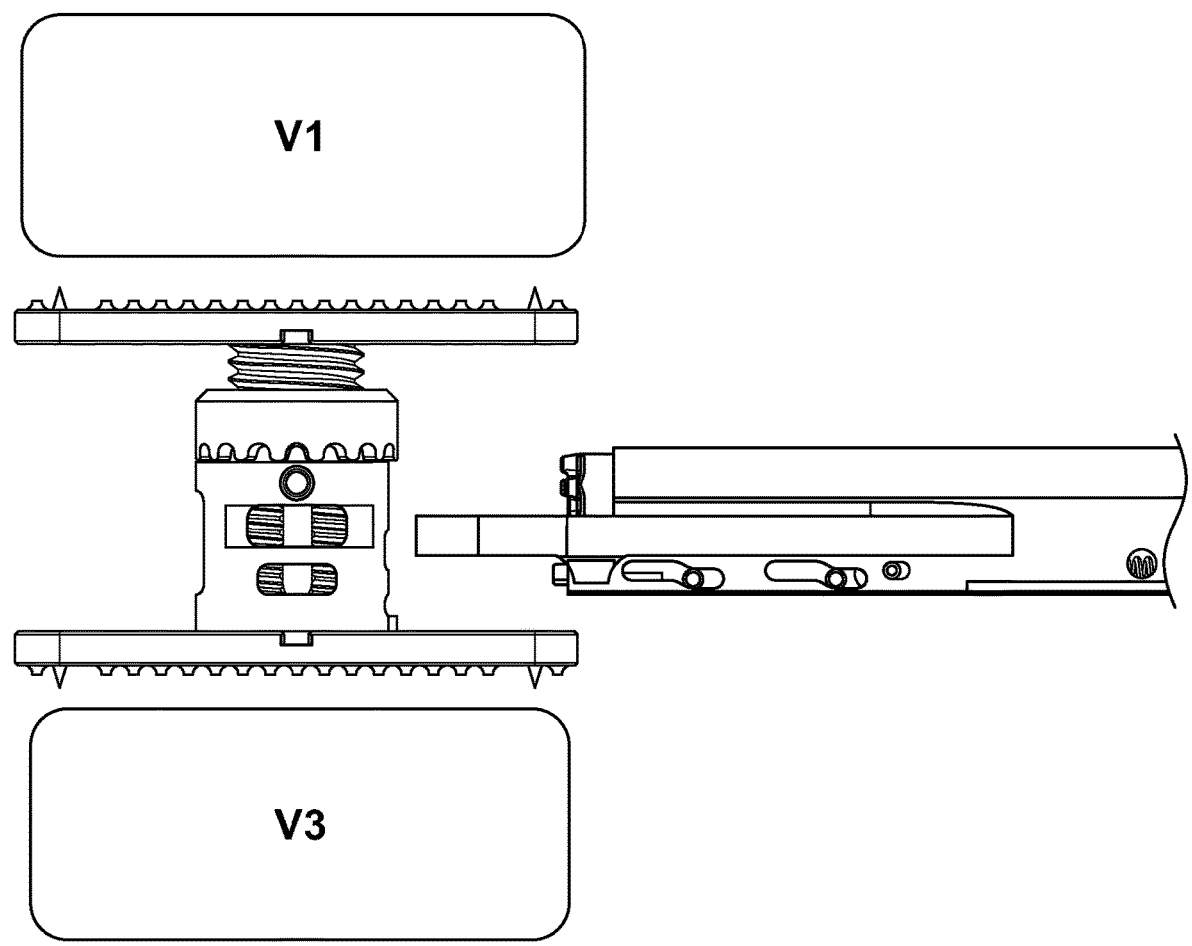

By way of example only, FIG. 28C illustrates the vertebral body implant assembly 10 being inserted in its collapsed state from a lateral direction into the space remaining between the superior and inferior vertebral bodies using the expanding tool 200. While shown inserting from a lateral direction, the implant may also be inserted from an anterior approach, an anterior-lateral approach, a posterior approach or a posterior-lateral approach. To accommodate insertion from various approaches, the endplates 11 are coupled to the expandable body 12 in a position relative to the transverse axis of the expandable body 12 to facilitate the chosen approach. The height of the vertebral body implant assembly 10 is then increased by rotating the distal handle 201 which causes the adjustment ring 13 to rotate, as described above. Since the vertebral body implant assembly 10 is secured between the engagement arms 116, the adjustment features 131 of the shaft end 130 can engage the external features 21 of the adjustment ring 13 so that when the distal handle 201 and the elongated first shaft 144 rotate, the adjustment ring 13 rotates in concert. As detailed above, rotation of the adjustment ring 13 causes expansion of the vertebral body implant assembly 10, as shown in FIG. 28D. The vertebral body implant assembly 10 is expanded until its desired height has been achieved. It is also possible to rotate the distal handle 201 in the opposite direction in order to cause the vertebral body implant assembly 10 to decrease in height. Once the desired height has been achieved, the large bezel 140 is rotated in the direction to cause the retraction of the second shaft 144 and thereby the lowering of the extension piece 117 and engagement tip 118 to release the vertebral body implant assembly 10. The expanding tool 200 is then separated from the vertebral body implant assembly 10 so that at least one set screw 16 from the outer core 14 can be engaged into the outer wall of the inner core 15 in order to secure the expanded height of the vertebral body implant assembly 10. Additional bone growth promoting material can then be added to the vertebral body implant assembly 10 before it is left to remain implanted between the first and second vertebrae.

While not specifically described above, it will be understood that various other steps may be performed in using and implanting the devices disclosed herein, including but not limited to creating an incision in a patient's skin, distracting and retracting tissue to establish an operative corridor to the surgical target site, advancing the implant through the operative corridor to the surgical target site, removing instrumentation from the operative corridor upon insertion of the implant, and closing the surgical wound.

While this invention has been described in terms of a best mode for achieving this invention's objectives, it will be appreciated by those skilled in the art that variations may be accomplished in view of these teachings without deviating from the spirit or scope of the invention.

What is claimed is:

1. An implant for providing support in a space remained after removal of at least part of a vertebra, comprising:
   an expandable body configured to expand from a first end to a second end along a longitudinal axis, the expandable body having an outer core and an inner core threadedly coupled and moveable relative to each other along the longitudinal axis, an adjustment ring rotatable about the longitudinal axis to adjust a relative location of the outer core to the inner core thereby adjusting a body length of the expandable body, a first attachment feature at the first end, and a second attachment feature at the second end;
   a first endplate coupled to the extendable body at the first end via the first attachment feature of the expandable body and a first matching attachment feature of the first endplate, the first matching attachment feature comprising a first receptacle configured to receive at least part of the first attachment feature along a transverse axis perpendicular to the longitudinal axis, wherein the first attachment feature of the expandable body includes a plurality of threaded holes disposed about a central aperture thereby allowing the first endplate to be coupled to the first end via the plurality of threaded holes in a plurality of rotational positions relative to the transverse axis; and
   a second endplate coupled to the expandable body at the second end via the second attachment feature and a second matching attachment feature, the second matching attachment feature comprising a second receptacle configured to receive at least part of the second attachment feature along the transverse axis perpendicular to the longitudinal axis.

2. The implant of claim 1, wherein the first receptacle comprises a groove, a flange, or both.

3. The implant of claim 2, wherein the groove, the flange, or both are extending along the transverse axis.

4. The implant of claim 2, wherein the first end comprises a first matching plate asymmetric about an axis perpendicular to the side of the first end.

5. The implant of claim 4, wherein the expandable body further comprises a threaded screw hole in the first matching plate and the first endplate further comprises a screw opening configured to align with the threaded screw hole to receive a set screw therethrough thereby locking the first endplate to the expandable body.

6. The implant of claim 1, wherein the first receptacle is configured to slidably receive the at least part of the first attachment feature along the transverse axis.

7. The implant of claim 5, wherein the screw opening is positioned along the transverse axis.

8. The implant of claim 1, wherein the adjustment ring is longitudinally coupled to the outer core.

9. The implant of claim 8, wherein the adjustment ring further comprises inner threads that couples to external threads of the inner core to cause longitudinal movement of the inner core relative to the outer core.

10. The implant of claim 1, wherein the adjustment ring further comprises external features evenly distributed along a circumference thereof and protruding along the longitudinal axis, the external features when engaged by proximal adjustment features of an inserter of the implant cause rotation of the adjustment ring in concert with rotation at a distal end of the inserter.

11. The implant of claim 1, wherein the first endplate and the second endplate are dimensioned to span from a lateral aspect of a vertebral body endplate to another lateral aspect of the vertebral body endplate.

12. An implant for providing support in a space remained after removal of at least part of a vertebra, comprising:
   an expandable body configured to expand from a first end to a second end along a longitudinal axis, the expandable body having an outer core and an inner core coupled and moveable to each other along the longitudinal axis, an adjustment ring rotatable about the longitudinal axis to adjust a relative position of the outer core to the inner core thereby adjusting a body length of the expandable body, a first attachment feature at the first end, and a second attachment feature at the second end;
   a first endplate slidably coupled to the expandable body at the first end via the first attachment feature of the expandable body and a first matching attachment feature of the first endplate, the first matching attachment feature comprising a first receptable configured to receive at least part of the first attachment feature along a transverse axis perpendicular to the longitudinal axis and an opening configured to align with the at least part of the first attachment feature for receiving a threaded fastener therethrough, wherein the first attachment feature of the expandable body includes a plurality of threaded holes disposed about a central aperture thereby allowing the first endplate to be coupled to the first end via the plurality of threaded holes in a plurality of rotational positions relative to the transverse axis; and
   a second endplate slidable coupled to the expandable body at the second end via the second attachment feature and a second matching attachment feature.

13. The implant of claim 12, wherein the first receptacle comprises a groove, a flange, or both.

14. The implant of claim 13, wherein the first end is asymmetric about an axis perpendicular to the side of the first end.

15. The implant of claim 12, wherein the opening is positioned along the transverse axis.

16. The implant of claim 12, wherein the adjustment ring is longitudinally coupled to the outer core.

17. The implant of claim 16, wherein the adjustment ring further comprises inner threads that couples to external threads of the inner core to cause longitudinal movement of the inner core relative to the outer core.

18. The implant of claim 12, wherein the adjustment ring further comprises external features evenly distributed along a circumference thereof and protruding along the longitudinal axis, the external features when engaged by proximal adjustment features of an inserter of the implant cause rotation of the adjustment ring in concert with rotation at a distal end of the inserter.

19. The implant of claim 12, wherein the first endplate and the second endplate are dimensioned to span from a lateral aspect of a vertebral body endplate to another lateral aspect of the vertebral body endplate.

20. An implant for providing support in a space remained after removal of at least part of a vertebra, comprising:
   an expandable body configured to expand along a longitudinal axis from a first end to a second end, the expandable body having an outer core and an inner core coupled and moveable relative to each other along the longitudinal axis, an adjustment ring rotatable about the longitudinal axis to adjust a relative location of the outer core to the inner core thereby adjusting a body length of the expandable body, a first attachment feature at the first end, and a second attachment feature at the second end,
   wherein the adjustment ring comprises external features evenly distributed along a circumference thereof and protruding along the longitudinal axis, the external features when engaged by proximal adjustment features of an inserter of the implant cause rotation of the adjustment ring in concert with rotation at a distal end of the inserter;
   a first endplate coupled to the expandable body at the first end via the first attachment feature and a first matching attachment feature, the first matching attachment feature comprising a first receptacle configured to receive at least part of the first attachment feature along a transverse axis perpendicular to the longitudinal axis, wherein the first attachment feature of the expandable body includes a plurality of threaded holes disposed about a central aperture thereby allowing the first endplate to be coupled to the first end via the plurality of threaded holes in a plurality of rotational positions relative to the transverse axis; and
   a second endplate coupled to the expandable body at the second end via the second attachment feature and a second matching attachment feature, the second matching attachment feature comprising a second receptacle configured to receive at least part of the second attachment feature along the transverse axis perpendicular to the longitudinal axis.

\* \* \* \* \*